US006420154B1

(12) United States Patent
Sheppard et al.

(10) Patent No.: US 6,420,154 B1
(45) Date of Patent: Jul. 16, 2002

(54) MAMMALIAN ADHESION PROTEASE PEPTIDES

(75) Inventors: Paul O. Sheppard, Granite Falls; Nand Baindur, Edmonds; Paul D. Bishop, Fall City, all of WA (US)

(73) Assignee: Zymogenetics, Inc., Seattle, WA (US)

( * ) Notice: Subject to any disclaimer, the term of this patent is extended or adjusted under 35 U.S.C. 154(b) by 0 days.

(21) Appl. No.: 09/632,098

(22) Filed: Aug. 2, 2000

Related U.S. Application Data

(60) Provisional application No. 60/146,968, filed on Aug. 3, 1999.

(51) Int. Cl.[7] .......................... C12N 9/48; C12N 1/20; C12N 15/00; C07H 21/04

(52) U.S. Cl. ................ 435/212; 435/252.3; 435/320.1; 536/23.2

(58) Field of Search ............................ 435/212, 252.3, 435/320.1; 536/23.2

(56) References Cited

PUBLICATIONS

Wolfsberg, et al., *Developmental Biology 169:* 378–383, 1995.
Wolfsberg, et al., *Developmental Biology 180:* 389–401, 1996.
Blobel, C., *Cell 90:*589–592, 1997.
Jia, et al., *J.Biol. Chem. 272:*13094–13102, 1997.
Barker, et al., *J. Med. Chem. 35:* 2040–2048, 1992.
AL117415; sequence ID:HSM801104 Blum, et al., 1999.
AL356755.12; sequence ID:AL356755, Sycamore, 2000.
Public EST 1997: EST, GenBank Accession No. AA442551.
Public EST 2000: EST, GenBank Accession No. AW796671
Incyte Pharmaceuticals, EST, 1996: INC946327.
Incyte Pharmaceuticals, EST, 1996: INC1371001.
Incyte Pharmaceuticals, EST, 1996: INC1252335.
Incyte Pharmaceuticals, EST, 1996: INC1479739.
Incyte Pharmaceuticals, EST, 1996: INC1508571.
Incyte Pharmaceuticals, EST, 1996: INC1501117.
Incyte Pharmaceuticals, EST, 1996: INC1960949.
Incyte Pharmaceuticals, EST, 1996: INC2082633.
Incyte Pharmaceuticals, EST, 1997: INC2313128.
Incyte Pharmaceuticals, EST, 1997: INC2265351.
Incyte Pharmaceuticals, EST, 1997: INC2524372.
Incyte Pharmaceuticals, EST, 1997: LIN1252335F6.
Incyte Pharmaceuticals, EST, 1997: INC2804841.
Incyte Pharmaceuticals, EST, 1997: INC2805142.
Incyte Pharmaceuticals, EST, 1997: INC2786453.
Incyte Pharmaceuticals, EST, 1997: INC2696821.
Incyte Pharmaceuticals, EST, 1997: INC2880287.
Incyte Pharmaceuticals, EST, 1997: INC2880533.
Incyte Pharmaceuticals, EST, 1997: INC3205125.
Incyte Pharmaceuticals, EST, 1997: INC3398729.
Incyte Pharmaceuticals, EST, 1997: INC3399285.
Incyte Pharmaceuticals, EST, 1997: INC2693639.
Incyte Pharmaceuticals, EST, 1997: INC3540126.
Incyte Pharmaceuticals, EST, 1997: INC3523825.
Incyte Pharmaceuticals, EST, 1997: INC3371248.
Incyte Pharmaceuticals, EST, 1997: INC3597305.
Incyte Pharmaceuticals, EST, 1997: INC3752335.
Incyte Pharmaceuticals, EST, 1997: INC3738507.
Incyte Pharmaceuticals, EST, 1997: INC3738465.
Incyte Pharmaceuticals, EST, 1997: INC3970085.
Incyte Pharmaceuticals, EST, 1998: INC3678903.
Incyte Pharmaceuticals, EST, 1998: INC3529607.
Incyte Pharmaceuticals, EST, 1998: INC4179758.
Incyte Pharmaceuticals, EST, 1998: INC4362070.
Incyte Pharmaceuticals, EST, 1998: INC4051909.
Incyte Pharmaceuticals, EST, 1998: INC4652558.
Incyte Pharmaceuticals, EST, 1998: INC4628047.
Incyte Pharmaceuticals, EST, 1998: INC4626906.
Incyte Pharmaceuticals, EST, 1998: INC4652386.
Incyte Pharmaceuticals, EST, 1998: INC5197377.
Incyte Pharmaceuticals, EST, 1998: INC4689928.
Incyte Pharmaceuticals, EST, 1998: INC4586217.
Incyte Pharmaceuticals, EST, 1999 (May): INC5866285.
Incyte Pharmaceuticals, EST, 1999 (Jul.): INC5560196.
Incyte Pharmaceuticals, EST, 1999 (Jul.): FLNSAOA00441F1.
Incyte Pharmaceuticals, EST, 1999 (Aug.): INC6009618.
Incyte Pharmaceuticals, EST, 1999 (Sep.): INC6394176.
Incyte Pharmaceuticals, EST, 1999 (Sep.): INC6427450.
Incyte Pharmaceuticals, EST, 1999 (Sep.): INC6299161.
Incyte Pharmaceuticals, EST, 2000 (Feb.): INC6958043.
Incyte Pharmaceuticals, EST, 2000 (Mar.): INC7015845.
Incyte Pharmaceuticals, EST, 2000 (Mar.): INC6831592.
Incyte Pharmaceuticals, EST, 2000 (Apr.): INC7254967.
Incyte Pharmaceuticals, EST, 2000 (Apr.): INC7230616.
Incyte Pharmaceuticals, EST, 2000 (Apr.): INC7249643.
Incyte Pharmaceuticals, EST, 2000 (May): INC7401354.
Incyte Pharmaceuticals, EST, 2000 (Jun.): INC7654635.
Incyte Pharmaceuticals, EST, 2000 (Jun.): INC7705839.
Incyte Pharmaceuticals, EST, 2000 (Jun.): INC7402592.
Incyte Pharmaceuticals, EST, 2000 (Jun.): INC7663110.
Incyte Pharmaceuticals, EST, 2000 (Jun.): INC7325424.
Incyte Pharmaceuticals, EST, 2000 (Jun.): INC7407422.
Incyte Pharmaceuticals, EST, 2000 (Jun.): INC7368174.
Incyte Pharmaceuticals, EST, 2000 (Jun.): INC7662132.

*Primary Examiner*—Ponnathapu Achutamurthy
*Assistant Examiner*—Yong Pak
(74) *Attorney, Agent, or Firm*—Robyn Adams

(57) ABSTRACT

The present invention relates to polynucleotide and polypeptide molecules, and variants thereof, for MAPP, a novel member of the Disintegrin Proteases. The polypeptides, and polynucleotides encoding them, are cell-cell interaction modulating and may be used for delivery and therapeutics. The present invention also includes antibodies to the MAPP polypeptides.

2 Claims, No Drawings

MAMMALIAN ADHESION PROTEASE PEPTIDES

REFERENCE TO RELATED APPLICATIONS

This application is related to Provisional Application 60/146,968 filed on Aug. 3, 1999. Under 35 U.S.C. § 119(e)(1), this application claims benefit of said Provisional Application.

BACKGROUND OF THE INVENTION

Disintegrins have been shown to bind cell surface molecules, including integrins, on the surface of various cells, such as platelets, fibroblasts, tumor, endothelial, muscle, neuronal, bone, and sperm cells. Disintegrins are unique and potentially useful tools for investigating cell-matrix and cell-cell interactions. Additionally, they have been useful in the development of antithrombotic and anti-metastatic agents due to their anti-adhesive, anti-migration of certain tumor cells, and anti-angiogenesis activities.

Families of proteins which have disintegrin domains include ADAMs (A Disintegrin and Metalloprotease), MDCs (Metalloprotease/Disintegrin/Cysteine-rich) and SVMPs (Snake Venom Metalloprotease).

For a review of ADAMs, see Wolfsberg and White, *Developmental Biology*, 180:389–401, 1996. ADAMs have been shown to exist as independent functional units as well as in conjunction with other members of this family in heterodimeric complexes. Some members of the family have multiple isoforms which may have resulted from alternative splicing. ADAMs proteins have been shown to have adhesive as well as anti-adhesive functions in their extracellular domains. Some members of the ADAMs family have very specific tissue distribution while others are widely distributed. Not all members of this family are capable of manifesting all of the potential functions represented by the domains common to their genetic structure.

The ADAMs are characterized by having a propeptide domain, a metalloprotease-like domain, a disintegrin-like domain, a cysteine-rich domain, an EGF-like domain, and a cytoplasmic domain.

A prototypical example of this family is ADAM 12. ADAM 12, also known as meltrin a, has a truncated isoform, as well as a full-length isoform, and is involved in muscle cell fusion and differentiation (Gilpin et al., *J. Biol. Chem.* 273:157–166, 1998). Other ADAMs involved in fusion are ADAM 1, and ADAM 2 which form a heterodimer (fertilin) and are involved in sperm/egg fusion (Wolfsberg and White, supra).

The SVMP family is represented by three classes (P-I, P-II, and P-III). All three classes contain propeptide and metalloprotease domains. The P-II and P-III classes also contain a disintegrin domain, and the P-III class further contains a cysteine-rich domain. These domains are similar in sequence to those found in the ADAMs. Some members of the SVMP family have a conserved “RGD” amino acid sequence. This tripeptide has been shown to form a hairpin loop whose conformation can disrupt the binding of fibrinogen to activated platelets. This “RGD” sequence may be substituted by RSE, MVD, MSE, and KGD in P-II SVMPs, and by MSEC (SEQ ID NO:14), RSEC (SEQ ID NO:15), IDDC (SEQ ID NO:16), and RDDC (SEQ ID NO:17) (a tripeptide along with a carboxy-terminal cysteine residue) in P-III SVMPs. Thus, these sequences may be responsible for integrin binding in the P-II and P-III SVMPs.

A prototypical example of a SVMP is jararhagin, which mediates platelet aggregation by binding to the platelet $a_2$ subunit (GPIa) via the disintegrin domain followed by proteolysis of the $b_1$ subunit (GPIIA) (Huang and Liu, *J. Toxicol-Toxin Reviews* 16: 135–161, 1997).

The proteins of the Metalloprotease/Disintegrin/Cysteine-rich family are involved in diverse tasks, ranging from roles in fertilization and muscle fusion, TNFa release from plasma membranes, intracellular protein cleavage, and essential functions in neuronal development (Blobel, C. P. *Cell* 90:589–592, 1997). This family is also characterized by the metalloprotease, disintegrin and cysteine-rich domains, as described above.

Members of the DP family of proteins which have been shown to be therapetuically useful include eptifibatide (Integrilin®, made by COR Therapeutics, Inc. and Key Pharmaceuticals, Inc.) which is useful as an anti-clotting agent for acute coronary syndrome, and contortrostatin, which inhibits $\beta_1$Integrin-mediated human metastatic melanoma cell adhesion and blocks experimental metastasis (Trikha, M. et at., *Cancer Research* 54: 4993–4998, 1994) and inhibits platelet aggregation (Clark, E. A. et al., *J. Biol. Chem.* 269 (35):21940–21943, 1994).

The present invention provides a novel member of the Disintegrin Proteases and related compositions whose uses will be apparent to those skilled in the art from the teachings herein.

SUMMARY OF THE INVENTION

Within one aspect the invention provides an isolated polypeptide molecule comprising residues 475 to 488 of SEQ ID NO:2. Within an embodiment, the isolated polypeptide molecule has one amino acid substitution. Within another embodiment, the isolated polypeptide molecule has two amino acid substitutions. Within another embodiment, the isolated polypeptide molecule comprises residues 420 to 495 of SEQ ID NO:2. Within another embodiment, the isolated polypeptide molecule is selected from the group consisting of: a) a polypeptide molecule comprising residues 208 to 495 of SEQ ID NO:2; b) a polypeptide molecule comprising residues 31 to 495 of SEQ ID NO:2; c) a polypeptide molecule comprising residues 1 to 495 of SEQ ID NO:2; d) a polypeptide molecule comprising residues 1 to 802 of SEQ ID NO:2; and e) a polypeptide molecule comprising residues 1 to 812 of SEQ ID NO:4. Within another embodiment, the invention provides an isolated polynucleotide molecule encoding the polypeptide. Within another embodiment, the invention provides the isolated polypeptide molecule comprising residues 475 to 488 of SEQ ID NO:2, wherein at least nine contiguous amino acid residues of SEQ ID NO:2 or SEQ ID NO:4 are operably linked via a peptide bond or polypeptide linker to a second polypeptide selected from the group consisting of maltose binding protein, an immunoglobulin constant region, and a polyhistidine tag.

Within another aspect, the invention provides an isolated polypeptide molecule, wherein the polypeptide molecule is selected from the group consisting of: a) a polypeptide molecule comprising residues 208 to 410 of SEQ ID NO:2; b) a polypeptide molecule comprising residues 497 to 802 of SEQ ID NO:2; c) a polypeptide molecule comprising residues 31 to 200 of SEQ ID NO:2; d) a polypeptide molecule comprising residues 497 to 701 of SEQ ID NO:4; e) a polypeptide molecule comprising residues 702 to 724 of SEQ ID NO:4; f) a polypeptide molecule comprising residues 725 to 812 of SEQ ID NO:4; g) a polypeptide molecule comprising residues 208 to 495 of SEQ ID NO:2; h) a polypeptide molecule comprising residues 31 to 495 of SEQ ID NO:2; i) a polypeptide molecule comprising residues 1 to 495 of SEQ ID NO:2; j) a polypeptide molecule comprising residues 208 to 802 of SEQ ID NO:2; k) a polypeptide molecule comprising residues 31 to 802 of SEQ ID NO:2; l) a polypeptide molecule comprising residues 1 to 802 of SEQ ID NO:2; m) a polypeptide molecule comprising residues 420 to 812 of SEQ ID NO:4; n) a polypeptide molecule comprising residues 204 to 812 of SEQ ID NO:4; o) a polypeptide molecule comprising residues 31 to 812 of SEQ ID NO:4; p) a polypeptide molecule comprising residues 1 to 812 of SEQ ID NO:4; q) a polypeptide molecule comprising residues 725 to 812 of SEQ ID NO:4; r) a polypeptide molecule comprising residues 497 to 724 of SEQ ID NO:4; s) a polypeptide molecule comprising residues 420 to 724 of SEQ ID NO:4; t) a polypeptide molecule comprising residues 208 to 724 of SEQ ID NO:4; u) a polypeptide molecule comprising residues 31 to 724 of SEQ ID NO:4; and v) a polypeptide molecule comprising residues 1 to 724 of SEQ ID NO:4. Within an embodiment is provided an isolated polynucleotide molecule encoding the polypeptide. Within an embodiment, is provided an expression vector comprising the following operably linked elements: a transcription promoter; a DNA segment encoding the polypeptide; and a transcription terminator. Within an embodiment, the DNA segment further encodes an affinity tag. Within another embodiment, the expression vector is introduced into a cultured cell and the cell expresses the polypeptide encoded by the DNAsegment. Within a further embodiment, the invention provides a method of producing a polypeptide comprising culturing the cell, whereby the cell expresses the polypeptide encoded by the DNA segment; and recovering the polypeptide. Within another embodiment, the invention provides the polypeptide produced by this method.

Within another aspect is provided isolated polypeptide molecules, and the polynucleotide molecules encoding them, wherein the polypeptide molecules comprise a contiguous sequence of amino acids, wherein the contiguous sequence of amino acids is selected from the group consisting of: residues 3 to 10; residues 153 to 162; residues 143 to 168; residues 179 to 188; residues 196 to 211; residues 225 to 236; residues 263 to 274; residues 284 to 297; residues 430 to 439; residues 550 to 561; residues 637 to 650; residues 712 to 719; residues 754 to 763; and residues 781 to 802, all of SEQ ID NO:2; and residues 679 to 700; residues 735 to 756; residues 748 to 756; residues 775 to792; and residues 797 to 806 all of SEQ ID NO:4 and residues 82 to 100; residues 109 to 123; residues 145 to 167; residues 179 to 188; residues 195 to 211; residues 223 to 238; residues 262 to 274; 286 to 297; residues 390 to 398; residues 430 to 439; residues 520 to 537; residues 550 to 561; residues 636 to 649; residues 712 to 719; residues 753 to 765; and residues 781 to 802 all of SEQ ID NO:2; and residues 662 to 671; residues 678 to 699; residues 729 to 759; and residues 769 to 807 all of SEQ ID NO:4.

Within another aspect, the invention provides a method of producing an antibody to the polypeptide manufactured by the method described above, comprising the following steps: inoculating an animal with the polypeptide such that the polypeptide elicits an immune response in the animal to produce the antibody; and isolating the antibody from the animal. Within an embodiment, the antibody produced by this method binds to a polypeptide of SEQ ID NOs:2 or 4. Within another embodiment, the invention provides an antibody which specifically binds to a polypeptide comprising amino acid residues 475 to 488 of SEQ ID NO:2.

Within another aspect, the invention provides a method for modulating cell-cell interactions comprising combining the cells with a polypeptide selected from the group consisting of: a) a polypeptide comprising residues 475 to 488 of SEQ ID NO:2; b) a polypeptide comprising residues 420 to 495 of SEQ ID NO:2; c) a polypeptide comprising residues 208 to 410 of SEQ ID NO:2; d) a polypeptide comprising residues 497 to 802 of SEQ ID NO:2; e) a polypeptide comprising residues 31 to 200 of SEQ ID NO:2; f) a polypeptide comprising residues 497 to 701 of SEQ ID NO:4; g) a polypeptide comprising residues 702 to 724 of SEQ ID NO:4; and h) a polypeptide comprising residues 725 to 812 of SEQ ID NO:4, whereby the cells come in contact with the polypeptide. Within an embodiment the cells are derived from tissues selected from the group consisting of: a) tissues from testes; b) tissues from ovary; c) tissues from spinal cord; d) tissues from prostate; e) tissues from small intestine; and f) tissues from colon.

Within another aspect the invention provides an isolated polypeptide, wherein the polypeptide comprises residues 208 to 410 of SEQ ID NO:2. Within an embodiment the polynucleotide encoding the polypeptide is provided.

Within one aspect, the present invention provides an isolated polypeptide molecule selected from the group consisting of: a) a polypeptide comprising a contiguous sequence of fourteen amino acids of SEQ ID NO:2; and b) polypeptide comprising a contiguous sequence of 14 amino acids of SEQ ID NO:4. Within an embodiment, the polypeptide molecule is between 78 and 305 amino acids in length.

Within another aspect, the invention provides an isolated polypeptide molecule selected from the group consisting of: a polypeptide molecule comprising residues 31 to 200 of SEQ ID NO:2; a polypeptide molecule comprising residues 208 to 410 of SEQ ID NO:2; a polypeptide molecule comprising residues 475 to 488 of SEQ ID NO:2; a polypeptide molecule comprising residues 420 to 495 of SEQ ID NO:2; a polypeptide molecule comprising residues 497 to 802 of SEQ ID NO:2; a polypeptide molecule comprising residues 31 to 802 of SEQ ID NO:2; a polypeptide molecule comprising residues 208 to 495 of SEQ ID NO:2; a polypeptide molecule comprising residues 208 to 802 of SEQ ID NO:2; a polypeptide molecule comprising residues 497 to 701 of SEQ ID NO:4; a polypeptide molecule comprising residues 702 to 724 of SEQ ID NO:4; a polypeptide molecule comprising residues 725 to 812 of SEQ ID NO:4; a polypeptide molecule comprising residues 204 to 701 of SEQ ID NO:4; a polypeptide molecule comprising residues 204 to 724 of SEQ ID NO:4; a polypeptide molecule comprising residues 31 to 812 of SEQ ID NO:4; a polypeptide molecule comprising residues 1 to 812 of SEQ ID NO:4; and a polypeptide molecule comprising residues 1 to 802 of SEQ ID NO:2.

Within another aspect, the invention provides an isolated polynucleotide molecule encoding a polypeptide molecule, wherein the polypeptide molecule comprises a contiguous sequence of fourteen amino acids of SEQ ID NO:2. Within an embodiment, the polypeptide molecule comprises residues 475 to 488 of SEQ ID NO:2. Within another embodiment, the polypeptide molecule is between 78 and 305 amino acids in length.

Within another aspect, the invention provides an isolated polynucleotide encoding a fusion protein comprising a first polypeptide segment and a second polypeptide segment, wherein the first polypeptide segment comprises a protease domain and the second polypeptide segment comprises a contiguous sequence of fourteen amino acids between residues 419 and 495 of SEQ ID NO:2, and wherein the first polypeptide segment is positioned amino-terminally to the second polypeptide segment. Within an embodiment, the protease domain is selected from the group consisting of; a protease domain that is a member of the Disintegrin Proteases; and a protease domain that is at least 80%, at least 90%, at least 95%, or at least 97% identical to amino acid residues 208 to 410 of SEQ ID NO:2.

Within another aspect, the invention provides an isolated polynucleotide encoding a fusion protein comprisisng a first polypeptide segment and a second polypeptide segment, wherein the first polypeptide segment comprises a first a contiguous sequence of 14 amino acids between residues 208 and 410 of SEQ ID NO:2, and the second polynpeptide segment comprises a disintegrin domain, and wherein the first polypeptide segment is positioned amino-terminally to the second polypeptide segment. Within an embodiment, the disintegrin domain is selected from the group consisting of; a disintegrin domain that is a member of the Disintegrin Proteases; and a disintegrin domain that is at least 80%, at least 90%, at least 95%, or at least 97% identical to amino acid residues 420 to 495 of SEQ ID NO:2.

Within another aspect, the invention provides an isolated polynucleotide molecule encoding a polypeptide molecule wherein the polynucleotide molecule is selected from the group consisting of: a polynucleotide molecule that encodes a polypeptide molecule that is at least 80%, at least 90%, at least 95%, or at least 97% identical to residues 208 to 410 of SEQ ID NO:2; and a polynucleotide molecule that is complementary to residues 208 to 410 of SEQ ID NO:2.

Within another aspect, the isolated polynucleotide molecule is selected from the group consisting of: a polynucleotide molecule that encodes a polypeptide molecule that is at least 80%, at least 90%, at least 95%, or at least 97% identical to residues 31 to 207 of SEQ ID NO:2; and a polynucleotide molecule that is complementary to residues 31 to 207 of SEQ ID NO:2.

Within another aspect, the isolated polynucleotide molecule is selected from the group consisting of: a polynucleotide molecule that encodes a polypeptide molecule that is at least 80%, at least 90%, at least 95%, or at least 97% identical to residues 1 to 802 of SEQ ID NO:2; a polynucleotide molecule that encodes a polypeptide molecule that is at least 80% identical to residues 1 to 812 of SEQ ID NO:4 and a polynucleotide molecule that is complementary residues 1 to 802 of SEQ ID NO:2.

These and other aspects of the invention will become evident upon reference to the following detailed description of the invention and attached drawings.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952A, 1985) (SEQ ID NO:7), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function (s) of the sequences are retained.

The term "ortholog" or "species homolog", denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based upon the discovery of novel cDNA sequences (SEQ ID NOs:1 and 3) and corresponding polypeptides having homology to disintegrin-like family members (ADAMs, SVMPs and MDCs; referred to herein as Disintegrin Proteases, or "DPs"). See, for example, Blobel, C. P., *Cell* 90:589–592, 1997, and Wolfsberg and White, *Developmental Biology* 180:389–401, 1996. Disintegrins can be involved in, for example, anticoagulation, fertilization, muscle fusion, and neurogenesis. Polynucleotides and polypeptides of the present invention have been designated Mammalian Adhesion Protease Peptides (MAPP), also termed herein, "zdint2".

A discussion of the domain structure of some members of the DPs will aid to illustrate the present invention in better detail. The secretory peptide has been described above.

The propeptide domain is usually amino-terminal to the metalloprotease domain and is can act as, an inhibitor for the metalloprotease domain (presumably via a cysteine-switch mechanism), such that the metalloprotease domain is activated in certain circumstances. This inhibition can be by blocking the active site of the metalloprotease domain.

The protease domain may be active or inactive. Some members of the disintegrin family have "active" zinc catalytic sites, which may be regulated by a "cysteine-switch" in the cysteine-rich domain. Examples of family members which have "active" protease domains are ADAM 1 and ADAM 10, which are involved in sperm/egg fusion and degradation of myelin basic sheath protein, respectively. Members of this family which do not have such a catalytic site include, for example, ADAM 11, which may be involved in tumor suppression. Other protein families which are know to have inactive protease domains are the serine proteases.

The adhesion (disintegrin) domain binds integrins or cell surface receptors which can be located on the surface of a multitude of cells, depending on the specificity of the disintegrin. The predicted binding site within this disintegrin domain is often an amino acid loop comprising about 13 to 14 amino acids. See Wolfsbeg and White, supra) The conformation of this sequence upon folding results in a hairpin loop presenting an amino acid sequence at its tip. This sequence is often "RGD", but may be substituted by a variety of other amino acid residues (Wolfsberg and White, supra; and Jia, *J. Biol. Chem.* 272:13094–13102, 1997). The diversity of these sequences may reflect that: 1) not all disintegrin domains serve as ligands for integrins (or other cell surface receptors); 2) disintegrin domains with different sequences bind to different types of integrins or cell surface receptors; or 3) the important part of the disintegrin loop is its structure, not its sequence, and thus, that the integrins or receptors for the specific classes of disintegrin domains can recognize a multitude of disintegrin binding loop sequences. Disintegrin domains have been shown to be responsible for cell-cell interactions, including inhibition of platelet aggregation by binding GPIIb/IIIa (fibronectin receptor) and/or GPIa/IIa (collagen receptor).

Many disintegrin family members have a fusion domain, a relatively hydrophobic domain of about 23 amino acids. This domain is present within some of the ADAM family members, and has been shown to be involved in cell-cell fusion, and particularly in sperm/egg fusion, and muscle fusion.

The cysteine-rich domain varies in the DP family members and is believed to be involved in structurally presenting the integrin-binding region to integrins. For the disintegrin-like members of this family, the cysteine-rich domain may also be necessary for secondary structure conformation of the polypeptide, specifically, disulfide bonding between the disintegrin domain and the cysteine domain.

Many DP family members have a transmembrane domain, which acts to anchor the polypeptide to the cell membrane. Membrane-anchored DPs can be involved in a process called "protein ectodomain shedding" wherein the metalloprotease domain cleaves extracellular domain(s) of another protein. In these cases, the metalloprotease can be active on the cell surface itself, as in the case of fertilin (ADAMs 1 and 2), or TACE (ADAM 17), or the metalloprotease can act intracellularly in the secretory pathway as has been described for KUZ and ADAM 10 (Blobel, C. P., supra; and Lammich, S. et al., *Proc. Natl. Acad. Sci. USA* 96:3922–3927, 1999, respectively). These membrane-anchored metalloproteases are likely to be active in the tissues where their genes are transcribed, in which cases they can be acting in cis, on other proteins bound to the same cell surface, in trans, on proteins bound to other cell surfaces, or on other proteins which are not membrane bound. Additionally the membrane anchor itself can be cleaved resulting in a soluble form of the metalloprotease/disintegrin which can be active at other sites in the body.

The cytoplasmic, or signaling, domain of disintegrin family members tends to be conserved in length and sites for phosphorylation. However, beyond that they tend to be unique in amino acid composition. Some disintegrin family members may signal by binding to the SH3 domain of Abl, Src, and/or Src-related SH3 domains.

Examination of the MAPP deduced amino acid sequence (SEQ ID NOs:2 and 4) permitted identification of two variants. The first variant has the following domains: a secretory peptide domain, beginning with residue 1 and ending with residue 24, 25, 26, 27, 28, 29 or 30 of SEQ ID NO:2; a putative propeptide domain, beginning with residue 28, 29, 30 or 31 and ending with residue 200, 203, 205 or 207 of SEQ ID NO:2; a protease domain, beginning with residue 204 or 208 and ending with residue 410 or 419 of SEQ ID NO:2; a disintegrin domain, beginning with residue 419 or 420 and ending with residue 495 or 496 of SEQ ID NO:2; and a cysteine-rich domain, beginning with residue 496 or 497 and ending with residue 802 of SEQ ID NO:2. Within the disintegrin domain, there is a "disintegrin loop" domain, residues 475 to 488 of SEQ ID NO:2. The amino acid sequence DCD, which corresponds to residues 481 to 483 of SEQ ID NO:2, is analogous to the "RGD binding loop" of some other members of the DPs. Within the protease domain is an active zinc catalytic site from residue 345 to residue 356 of SEQ ID NO:2.

The second variant shares the signal, putative propeptide, metalloprotease, and disintegrin domains with the first variant. The polynucleotide and polypeptide sequences for the second variant are shown in SEQ ID NOs:3 and 4, respectively. The polypeptide sequence of the second variant diverges from the sequence of the first variant (SEQ ID NO:2) beginning in the cysteine-rich domain. Thus, it has the polynucleotide and polypeptide sequence of the first variant from residues 1 to 661 of SEQ ID NOs:2 and 4. Additionally, the second variant has a transmembrane domain and a cytoplasmic domain. The cysteine-rich domain begins with residue 496 or 497 and ends with residue 701 of SEQ ID NO:4. The transmembrane domain begins with residue 702 and ends with residue 724 of SEQ ID NO:4. The cytoplasmic domain begins with residue 725 and ends with residue 812 of SEQ ID NO:4.

Analysis of the tissue distribution of MAPP was performed by the Northern blotting technique using a Human Multiple Tissue blot (CLONTECH Laboratories, Inc., Palo Alto, Calif.) and resulted in a single transcript of ~4.4 kb with a strong signal in testes, ovary, prostate, small intestine, and colon and a fainter signal in stomach, thyroid, spinal cord, lymph node, and trachea. Also on the Multiple Tissue Northern there were two transcripts, ~4.0 kb and ~4.4 kb, both of medium signal strength in heart tissue. A RNA Master Dot Blot indicated faint signals in many tissues with strong signals in spinal cord, heart, aorta, colon, bladder, small intestine, uterus, prostate, stomach, testis, ovary, mammary gland, appendix, lung, trachea, fetal lung, and placenta.

Some members of the DP family have alternatively spliced isoforms. Thus, the first variant (SEQ ID NO:2) and second variant (SEQ ID NO:4) of zdint2 are alternatively spliced products of the same gene. Another protein which is an example of alternative splicing in the DPs is ADAM 12, also known as meltrin a. The truncated form of this molecule, which lacks the propeptide and metalloprotease domains, is associated with ectopic muscle formation in vivo, but not in vitro, indicating that cells expressing this gene produce a growth factor that acts on neighboring progenitor cells.

The present invention provides polynucleotide molecules, including DNA and RNA molecules, that encode the MAPP polypeptides disclosed herein. Those skilled in the art will readily recognize that, in view of the degeneracy of the genetic code, considerable sequence variation is possible among these polynucleotide molecules. SEQ ID NO:5 is a degenerate DNA sequence that encompasses all DNAs that encode the MAPP polypeptide of SEQ ID NO:2. SEQ ID NO:6 is a degenerate DNA sequence that encompasses all DNAs that encode the MAPP polypeptide of SEQ ID NO:4. Those skilled in the art will recognize that the degenerate sequence of SEQ ID NOs:5 and 6 also provides all RNA sequences encoding SEQ ID NOs:2 and 4 by substituting U for T. Thus, MAPP polypeptide-encoding polynucleotides comprising nucleotide 1 to nucleotide 2406 of SEQ ID NO:5, and comprising nucleotide 1 to nucleotide 2439 of SEQ ID NO:6, and their RNA equivalents are contemplated by the present invention. Table 1 sets forth the one-letter codes used within SEQ ID NOs:5 and 6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:5 and 6, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |

TABLE 2-continued

| Amino Acid | One Letter Code | Codons | Degenerate Codon |
|---|---|---|---|
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:5 and 6 serve as templates for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NOs:1 and 3, or a sequence complementary thereto under stringent conditions. Polynucleotide hybridization is well known in the art and widely used for many applications, see for example, Sambrook et al., *Molecular Cloning: A Laboratory Manual, Second Edition*, Cold Spring Harbor, N.Y., 1989; Ausubel et al., eds., *Current Protocols in Molecular Biology*, John Wiley and Sons, Inc., N.Y., 1987; Berger and Kimmel, eds., Guide to Molecular Cloning Techniques, *Methods in Enzymology*, volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

As an illustration, a nucleic acid molecule encoding a variant MAPP polypeptide can be hybridized with a nucleic acid molecule having the nucleotide sequence of SEQ ID NOs:1 or 3 (or their complements) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., ExpressHyb™ Hybridization Holution from CLONTECH Laboratories, Inc., Palo Alto, Calif.) according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant MAPP polypeptide hybridize with a nucleic acid molecule having the nucleotide sequences of SEQ ID NOs:1 or 3 (or their complements) under stringent washing conditions, in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

The present invention also contemplates MAPP variant nucleic acid molecules that can be identified using two criteria: a determination of the similarity between the encoded polypeptides with the amino acid sequence sof SEQ ID NOs:2 and 4 (as described below), and a hybridization assay, as described above. Such MAPP variants include nucleic acid molecules (1) that hybridize with a nucleic acid molecule having the nucleotide sequence of SEQ ID NOs:1 or 3 (or thier complements) under stringent washing conditions, in which the wash stringency is equivalent to 0.5×–2×SSC with 0.1% SDS at 55–65° C., and (2) that encode a polypeptide having at least 80%, preferably 90%, more preferably, 95% or greater than 95% sequence identity to the amino acid sequence of SEQ ID NOs:2 or 4. Alternatively, MAPP variants can be characterized as nucleic acid molecules (1) that hybridize with a nucleic acid molecule having the nucleotide sequence of SEQ ID NOs:1 or 3 (or their complements) under highly stringent washing conditions, in which the wash stringency is equivalent to 0.1×–0.2×SSC with 0.1% SDS at 50–65° C., and (2) that encode a polypeptide having at least 80%, preferably 90%, more preferably 95% or greater than 95% sequence identity to the amino acid sequence of SEQ ID NOs:2 or 4.

The highly conserved amino acids in the disintegrin domain of MAPP can be used as a tool to identify new family members. For instance, reverse transcription-polymerase chain reaction (RT-PCR) can be used to amplify sequences encoding the conserved disintegrin domain from RNA obtained from a variety of tissue sources or cell lines. In particular, highly degenerate primers designed from the MAPP sequences are useful for this purpose.

As previously noted, the isolated polynucleotides of the present invention include DNA and RNA. Methods for preparing DNA and RNA are well known in the art. In general, RNA is isolated from a tissue or cell that produces large amounts of MAPP RNA. Such tissues and cells are identified by Northern blotting (Thomas, *Proc. Natl. Acad. Sci. USA* 77:5201, 1980), and include testes, ovary, prostate, small intestine, colon, spinal cord, heart, aorta, bladder, uterus, stomach, mammary gland, appendix, lung, trachea, fetal lung, and placenta.

Total RNA can be prepared using guanidine isothiocyante extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. In the alternative, genomic DNA can be isolated. Polynucleotides encoding MAPP polypeptides are then identified and isolated by, for example, hybridization or PCR.

A full-length clone encoding MAPP can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to MAPP or other specific binding partners.

MAPP polynucleotide sequences disclosed herein can also be used as probes or primers to clone 5' non-coding regions of a MAPP gene. In view of the tissue-specific expression observed for MAPP by Northern blotting, this gene region is expected to provide for specific expression in testes, ovary, prostate, small intestine, colon, spinal cord, heart, aorta, bladder, uterus, stomach, mammary gland, appendix, lung, trachea, fetal lung, and placenta. Promoter elements from a MAPP gene could thus be used to direct the tissue-specific expression of heterologous genes in, for example, transgenic animals or patients treated with gene therapy. Cloning of 5' flanking sequences also facilitates production of MAPP proteins by "gene activation" as disclosed in U.S. Pat. No. 5,641,670. Briefly, expression of an endogenous MAPP gene in a cell is altered by introducing into the MAPP locus a DNA construct comprising at least a targeting sequence, a regulatory sequence, an exon, and an unpaired splice donor site. The targeting sequence is a MAPP 5' non-coding sequence that permits homologous recombination of the construct with the endogenous MAPP locus, whereby the sequences within the construct become operably linked with the endogenous MAPP coding sequence. In this way, an endogenous MAPP promoter can be replaced or supplemented with other regulatory sequences to provide enhanced, tissue-specific, or otherwise regulated expression.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323–356 (1984) and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are MAPP polypeptides from other mammalian species, including murine, porcine, ovine, bovine, canine, feline, equine, and other primate polypeptides. Orthologs of human MAPP can be cloned using information and compositions provided by the present invention in combination with conventional cloning techniques. For example, a cDNA can be cloned using mRNA obtained from a tissue or cell type that expresses MAPP as disclosed herein. Such tissue would include, for example, testes, ovary, prostate, small intestine, colon, spinal cord, heart, aorta, bladder, uterus, stomach, mammary gland, appendix, lung, trachea, fetal lung, and placenta. Suitable sources of mRNA can be identified by probing Northern blots with probes designed from the sequences disclosed herein. A library is then prepared from mRNA of a positive tissue or cell line. A MAPP-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human MAPP sequences disclosed herein. Within an additional method, the cDNA library can be used to transform or transfect host cells, and expression of the cDNA of interest can be detected with an antibody to MAPP polypeptide. Similar techniques can also be applied to the isolation of genomic clones.

Those skilled in the art will recognize that the sequences disclosed in SEQ ID NOs:1 and 3 represent a single allele of human MAPP and that allelic variation and alternative splicing are expected to occur. Allelic variants of this sequence can be cloned by probing cDNA or genomic libraries from different individuals according to standard procedures. Allelic variants of the DNA sequences shown in SEQ ID NOs:1 and 3, including those containing silent mutations and those in which mutations result in amino acid sequence changes, are within the scope of the present invention, as are proteins which are allelic variants of SEQ ID NOs:2 and 4. cDNAs generated from alternatively spliced mRNAs, which retain the properties of the MAPP polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. As stated earlier, polynucleotides of SEQ ID NO:1 and SEQ ID NO:3 are alternatively spliced variants of the same gene.

The present invention also provides isolated MAPP polypeptides that are substantially similar to the polypeptides of SEQ ID NOs:2 and 4 and their orthologs. Such polypeptides will more preferably be at least 90% identical, and more preferably 95% or more identical to SEQ ID NOs:2 and 4 and their orthologs. The present invention also includes polypeptides that comprise an amino acid sequence having at at least 93%, preferably 95% or greater than 95% sequence identity to the disintegrin loop domain, residues 475 to 478 of SEQ ID NOs:2 and 4. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number identical matches}}{\left[\begin{array}{c}\text{length of the longer sequence plus the number of gaps introduced} \\ \text{into the longer sequence in order to align the two sequences}\end{array}\right]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant MAPP. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequences of SEQ ID NOs:2 and 4. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in an MAPP gene can be introduced by substituting nucleotides for the nucleotides recited in SEQ ID NOs:1 and 3. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The ability of such variants to promote cell-cell interactions can be determined using a standard method, such as the assay described herein. Alternatively, a variant MAPP polypeptide can be identified by the ability to specifically bind anti-MAPP antibodies. Additional amino acid substitutions which improve the activity of MAPP molecules of the present invention include the substitution of residue 482 (Cys) with alanine.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of disintegrin-integrin, or protease interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related disintegrin-like molecules.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed MAPP DNA and polypeptide sequences can be generated through DNA shuffling, as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., disintegrin-cell surface binding or protease activity) can be recovered from the host cells and rapidly sequenced using modem equipment. These methods allow the rapid determination of the importance of individual amino acid residues in a polypeptide of interest, and can be applied to polypeptides of unknown structure.

Regardless of the particular nucleotide sequence of a variant MAPP gene, the gene encodes a polypeptide that is characterized by its cell-cell interaction activity, or by the ability to bind specifically to an anti-MAPP antibody. More specifically, variant MAPP genes encode polypeptides which exhibit at least 50%, and preferably, greater than 70, 80, or 90%, of the activity of polypeptide encoded by the human MAPP gene described herein.

Variant MAPP polypeptides or substantially homologous MAPP polypeptides are characterized as having one or more amino acid substitutions, deletions or additions. These changes are preferably of a minor nature, that is conservative amino acid substitutions and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from 775 to 2000 amino acid residues that comprise a sequence that is at least 85%, preferably at least 90%, and more preferably 95% or more identical to the corresponding region of SEQ ID NOs:2 or 4. Polypeptides comprising affinity tags can further comprise a proteolytic cleavage site between the MAPP polypeptide and the affinity tag. Preferred such sites include thrombin cleavage sites and factor Xa cleavage sites.

For any MAPP polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise MAPP variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:4, SEQ ID NO:5, and SEQ ID NO:6. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention further provides a variety of other polypeptide fusions and related multimeric proteins comprising one or more polypeptide fusions. For example, a disintegrin polypeptide domain can be prepared as a fusion to a dimerizing protein, as disclosed in U.S. Pat. Nos. 5,155,027 and 5,567,584. Preferred dimerizing proteins in this regard include other disintegrin polypeptide domains, disintegrin polypeptide domain fragments, or polypeptides comprising other members of the Disintegrin Protease family of proteins, such as, for example, members of the MDCs, SVMPs, and ADAMs. These disintegrin polypeptide domain fusions, disintegrin polypeptide domain fragment fusions, or fusions with other Disintegrin Proteases can be expressed in genetically engineered cells to produce a variety of multimeric disintegrin-like analogs.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between MAPP of the present invention with the functionally equivalent domain(s) from another family member, such as ADAM, MDC, and SVMP. Such domains include, but are not limited to, conserved motifs such as the secretory signal sequence, propeptide, protease, disintegrin and disintegrin loop domains, including the "RGD" or "DCD" sequence, the cysteine, transmembrane, and signaling domains. Such fusion proteins would be expected to have a biological functional profile that is the same or similar to polypeptides of the present invention or other known disintegrin-like family proteins (e.g. ADAMs, MDCs, and SVMPs), depending on the fusion constructed. Moreover, such fusion proteins may exhibit other properties as disclosed herein.

Moreover, using methods described in the art, polypeptide fusions, or hybrid MAPP proteins, are constructed using regions or domains of the inventive MAPP in combination with those of other disintegrin and disintegrin-like molecules. (e.g. ADAM, MDC, and SVMP), or heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Auxiliary domains can be fused to MAPP polypeptides to target them to specific cells, tissues, or macromolecules (e.g., testes, ovary, prostate, small intestine, colon, spinal cord, heart, aorta, bladder, uterus, stomach, mammary gland, appendix, lung, trachea, fetal lung, and placenta). For example, a protease polypeptide domain, or protease polypeptide fragment or protein, could be targeted to a predetermined cell type by fusing it to a disintegrin polypeptide domain or fragment that specifically binds to an integrin polypeptide or integrin-like polypeptide on the surface of the target cell. In this way, polypeptides, polypeptide fragments and proteins can be targeted for therapeutic or diagnostic purposes. Such disintegrins or protease polypeptide domains or fragments can be fused to two or more moieties, such as an affinity tag for purification and a targeting-disintegrin domain. Polypeptide fusions can also comprise one or more cleavage sites, particularly between domains. See, Tuan et al., *Connective Tissue Research* 34:1–9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of MAPP polypeptide can be fused to *E. coli* β-galactosidase (1,021 residues; see Casadaban et al., J. Bacteriol. 143:971–980, 1980), a 10-residue spacer, and a 4-residue factor Xa cleavage site. In a second example, residues of MAPP polypeptide can be fused to maltose binding protein (approximately 370 residues), a 4-residue cleavage site, and a 6-residue polyhistidine tag.

To direct the export of a MAPP polypeptide from the host cell, the MAPP DNA is linked to a second DNA segment encoding a secretory peptide, such as a t-PA secretory peptide or a MAPP secretory peptide. To facilitate purification of the secreted polypeptide, a C-terminal extension, such as a poly-histidine tag, substance P, Flag peptide (Hopp et al., *Bio/Technology* 6:1204–1210, 1988; available from Eastman Kodak Co., New Haven, Conn.), maltose binding protein, or another polypeptide or protein for which an antibody or other specific binding agent is available, can be fused to the MAPP polypeptide.

The present invention also includes "functional fragments" of MAPP polypeptides and nucleic acid molecules encoding such functional fragments. Routine deletion analyses of nucleic acid molecules can be performed to obtain functional fragments of a nucleic acid molecule that encodes an MAPP polypeptide. As an illustration, DNA molecules having the nucleotide sequence of SEQ ID NOs:1 or 3 can be digested with Bal31 nuclease to obtain a series of nested deletions. The fragments are then inserted into expression vectors in proper reading frame, and the expressed polypeptides are isolated and tested for cell-cell interactions, or for the ability to bind anti-MAPP antibodies. One alternative to exonuclease digestion is to use oligonucleotide-directed mutagenesis to introduce deletions or stop codons to specify production of a desired fragment. Alternatively, particular fragments of an MAPP gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65–72 (Nijhoff 1987), Herschman, "The EGF Receptor," in *Control of Animal Cell Proliferation*, Vol. 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a MAPP gene that have amino acid changes, compared with the amino acid sequence of SEQ ID NOs:2 and 4. A variant MAPP gene can be identified on the basis of structure by determining the level of identity with nucleotide and amino acid sequences of SEQ ID NOs:1, 2, 3 and 4, as discussed above. An alternative approach to identifying a variant gene on the basis of structure is to determine whether a nucleic acid molecule encoding a potential variant MAPP gene can hybridize to a nucleic acid molecule having the nucleotide sequence of SEQ ID NOs:1 and 3, as discussed above.

Using the methods discussed herein, one of ordinary skill in the art can identify and/or prepare a variety of polypeptide fragments or variants of SEQ ID NOs:2 and 4 or that retain the disintegrin and/or metalloprotease activity of the wild-type MAPP protein. Such polypeptides may include additional amino acids from, for example, a secretory domain, a propeptide domain, a protease domain, a disintegrin domain, a disintegrin loop (native or synthetic), part or all of a transmembrane and intracellular domains, including amino acids responsible for intracellular signaling; fusion domains; affinity tags; and the like.

The present invention also provides polypeptide fragments or peptides comprising an epitope-bearing portion of an MAPP polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, preferably at least ten to fifteen amino acids, more preferably 15 to amino acids of SEQ ID NOs:2 and 4. Such epitope-bearing peptides and polypeptides can be produced by fragmenting a MAPP polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

As an illustration, potential antigenic sites in MAPP were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The results of this analysis indicated that a peptide consisting of amino acid residues 3 to 10 of SEQ ID NO:2; residues 55 to 64 of SEQ ID NO:2; residues 96 to 102 of SEQ ID NO:2; residues 153 to 162 of SEQ ID NO:2; residues 153 to 168 of SEQ ID NO:2; residues 143 to 168 of SEQ ID NO:2; residues 179 to 188 of SEQ ID NO:2; residues 177 to 189 of SEQ ID NO:2; residues 196 to 211 of SEQ ID NO:2; residues 225 to 236 of SEQ ID NO:2; residues 263 to 274 of SEQ ID NO:2; residues 284 to 297 of SEQ ID NO:2; residues 288 to 297 of SEQ ID NO:2; residues 318 to 334 of SEQ ID NO:2; residues 354 to 360 of SEQ ID NO:2; residues 365 to 371 of SEQ ID NO:2; residues 388 to 393 of SEQ ID NO:2; residues 397 to 403 of SEQ ID NO:2; residues 407 to 413 of SEQ ID NO:2; residues 428 to 441 of SEQ ID NO:2; residues 430 to 439 of SEQ ID NO:2; residues 449 to 463 of SEQ ID NO:2; residues 478 to 484 of SEQ ID NO:2; residues 489 to 497 of SEQ ID NO:2; residues 503 to 510 of SEQ ID NO:2; residues 533 to 539 of SEQ ID NO:2; residues 547 to 562 of SEQ ID NO:2; residues 550 to 561 of SEQ ID NO:2; residues 566 to 573 of SEQ ID NO:2; residues 577 to 584 of SEQ ID NO:2; residues 599 to 606 of SEQ ID NO:2; residues 626 to 633 of SEQ ID NO:2; residues 637 to 646 of SEQ ID NO:2; residues 637 to 650 of SEQ ID NO:2; residues 712 to 719 of SEQ ID NO:2; residues 754 to 763 of SEQ ID NO:2; and residues 781 to 802 of SEQ ID NO:2;

residues 783 to 802 of SEQ ID NO:2; and residues 679 to 700 of SEQ ID NO:4; residues 735 to 756 of SEQ ID NO:4; residues 735 to 759 of SEQ ID NO:4;, residues 748 to 756 of SEQ ID NO:4; residues 775 to 792 of SEQ ID NO:4; and residues 797 to 806 of SEQ ID NO:4 are antigenic peptides.

MAPP polypeptides can also be used to prepare antibodies that specifically bind to MAPP epitopes, peptides or polypeptides. The MAPP polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a MAPP polypeptide (e.g., SEQ ID NOs:2 and 4). Polypeptides comprising a larger portion of a MAPP polypeptide, i.e., from 30 to 10 residues up to the entire length of the amino acid sequence are included. Antigens or immunogenic epitopes can also include attached tags, adjuvants and carriers, as described herein. Suitable antigens include the MAPP polypeptides encoded by SEQ ID NO:2 from amino acid number 204 to amino acid number 802, or a contiguous 9 to 850 amino acid fragment thereof. Suitable antigens also include the MAPP polypeptides encoded by SEQ ID NO:4 from amino acid number 204 to amino acid number 812, or a contiguous 9 to 860 amino acid fragment thereof. Other suitable antigens include residue 1 to residue 24, 25, 26, 27, 28, 29, or of SEQ ID NO:2; residue 28, 29, 30, or 31 to residue 200, 203, 205, or 207 of SEQ ID NO:2; residue 204 or 208 to residue 410 or 419 of SEQ ID NO:2; residue 419 or 420 to residue 495 or 496 of SEQ ID NO:2; residue 496 or 497 to residue 802 of SEQ ID NO:2; residue 496 or 497 to residue 701 of SEQ ID NO:4; residue 702 to residue 724 of SEQ ID NO:4; and residue 725 to residue 812 of SEQ ID NO:4. Preferred peptides to use as antigens are hydrophilic peptides such as those predicted by one of skill in the art from a hydrophobicity plot. MAPP hydrophilic peptides include peptides comprising amino acid sequences selected from the group consisting of: residues 1 to 10 of SEQ ID NO:2; residues 45 to 55 of SEQ ID NO:2; residues 82 to 88 of SEQ ID NO:2; residues 82 to 100 of SEQ ID NO:2; residues 94 to 100 of SEQ ID NO:2; residues 109 to 123 of SEQ ID NO:2; residues 145 to 167 of SEQ ID NO:2; residues 179 to 188 of SEQ ID NO:2; residues 195 to 211 of SEQ ID NO:2; residues 223 to 238 of SEQ ID NO:2; residues 262 to 274 of SEQ ID NO:2; residues 286 to 297 of SEQ ID NO:2; residues 390 to 398 of SEQ ID NO:2; residues 430 to 439 of SEQ ID NO:2; residues 520 to 537 of SEQ ID NO:2; residues 550 to 561 of SEQ ID NO:2; residues 636 to 649 of SEQ ID NO:2; residues 712 to 719 of SEQ ID NO:2; residues 753 to 765 of SEQ ID NO:2; and residues 781 to 802 of SEQ ID NO:2; and residues 693 to 699 of SEQ ID NO:4; residues 662 to 671 of SEQ ID NO:4; residues 678 to 699 of SEQ ID NO:4; residues 729 to 759 of SEQ ID NO:4; residues 769 to 807 of SEQ ID NO:4. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a MAPP polypeptide or a fragment thereof. The immunogenicity of a MAPP polypeptide may be increased through the use of an adjuvant, such as alum (aluminum hydroxide) or Freund's complete or incomplete adjuvant. Polypeptides useful for immunization also include fusion polypeptides, such as fusions of MAPP or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to MAPP protein or peptide, and selection of antibody display libraries in phage or similar vectors (for instance, through use of immobilized or labeled MAPP protein or peptide). Genes encoding polypeptides having potential MAPP polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from CLONTECH Laboratories, Inc., (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the MAPP sequences disclosed herein to identify proteins which bind to MAPP. These "binding proteins" which interact with MAPP polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as MAPP "antagonists" to block MAPP binding and signal transduction in vitro and in vivo. These anti-MAPP binding proteins would be useful for modulating, for example, platelet aggregation, apoptosis, neurogenesis, myogenesis, immunologic recognition, tumor formation, and cell-cell interactions in general.

Antibodies are determined to be specifically binding if they exhibit a threshold level of binding activity (to a MAPP polypeptide, peptide or epitope) of at least 10-fold greater than the binding affinity to a control (non-MAPP) polypeptide. The binding affinity of an antibody can be readily determined by one of ordinary skill in the art, for example, by Scatchard analysis (Scatchard, G., *Ann. NY Acad. Sci.* 51: 660–672, 1949).

A variety of assays known to those skilled in the art can be utilized to detect antibodies which specifically bind to MAPP proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant MAPP protein or polypeptide.

Antibodies to MAPP may be used for tagging cells that express MAPP; for isolating MAPP by affinity purification; for diagnostic assays for determining circulating levels of MAPP polypeptides; for detecting or quantitating soluble MAPP as marker of underlying pathology or disease; in analytical methods employing FACS; for screening expression libraries; for generating anti-idiotypic antibodies; and as neutralizing antibodies or as antagonists to block MAPP in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to MAPP or fragments thereof may be used in vitro to detect denatured MAPP or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (integrin or antigen, respectively, for instance). More specifically, MAPP polypeptides or anti-MAPP antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer−+ cells or tissues). Alternatively, a fusion protein including only the disintegrin domain may be suitable for directing a detectable molecule, a cytotoxic molecule or a complementary molecule to a cell or tissue type of interest. Similarly, the corresponding integrin to MAPP can be conjugated to a detectable or cytotoxic molecule and provide a generic targeting vehicle for cell/tissue-specific delivery of generic anti-complementary-detectable/cytotoxic molecule conjugates.

In another embodiment, MAPP-cytokine fusion proteins or antibody-cytokine fusion proteins can be used for enhancing in vivo killing of target tissues (for example, testes, ovary, prostate, small intestine, colon, spinal cord, heart, aorta, bladder, uterus, stomach, mammary gland, appendix, lung, trachea, fetal lung, and placenta), if the MAPP polypeptide or anti-MAPP antibody targets hyperproliferative tissues from these organs. (See, generally, Hornick et al., *Blood* 89:4437–47, 1997). They described fusion proteins that enable targeting of a cytokine to a desired site of action, thereby providing an elevated local concentration of cytokine. Suitable MAPP polypeptides or anti-MAPP antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

In yet another embodiment, if the MAPP polypeptide or anti-MAPP antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

The MAPP polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a MAPP polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a MAPP polypeptide into the secretory pathway of a host cell, a secretory signal sequence (also known as a leader sequence, prepro sequence or pre sequence) is provided in the expression vector. The secretory signal sequence may be that of MAPP, or may be derived from another secreted protein (e.g., t-PA) or synthesized de novo. The secretory signal sequence is operably linked to the MAPP DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The native secretory signal sequence of the polypeptides of the present invention is used to direct other polypeptides into the secretory pathway. The present invention provides for such fusion polypeptides. A signal fusion polypeptide can be made wherein a secretory signal sequence derived from a MAPP polypeptide is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Alternatively, the protease domain of MAPP can be substituted by a heterologous sequence providing a different protease domain. In this case, the fusion product can be secreted, and the disintegrin domain of MAPP can direct the protease domain to a specific tissue described above. This substituted protease domain can be chosen from the protease domains represented by the DP protein families, or domains from other known proteases. Similarly, the disintegrin domain of MAPP protein can be substituted by a heterlogous sequence providing a different disintegrin domain. Again, the fusion product can be secreted and the substituted disintegrin domain can target the protease domain of MAPP to a specific tissue. The substituted disintegrin domain can be chosen from the disintegrin domains of the DP protein families. In these cases, the fusion products can be soluble or membrane-anchored proteins.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification-." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of

*Agrobacterium rhizogenes* as a vector for expressing genes in plant cells has been reviewed by Sinkar et al., *J. Biosci.* (*Bangalore*) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from Autographa califomica nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant MAPP baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the MAPP polypeptide into a baculovirus genome maintained in *E. coli* as a large plasmid called a "bacmid." The pFastBac1™ transfer vector utilizes the AcNPV polyhedrin promoter to drive the expression of the gene of interest, in this case MAPP. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol Chem* 270:1543–9, 1995. In such transfer vector constructs, a short or long version of the basic protein promoter can be used. Moreover, transfer vectors can be constructed which replace the native MAPP secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native MAPP secretory signal sequence. In addition, transfer vectors can include an in-frame fusion with DNA encoding an epitope tag at the C- or N-terminus of the expressed MAPP polypeptide, for example, a Glu-Glu epitope tag (Grussenmeyer, T. et al., *Proc. Natl. Acad. Sci.* 82:7952–4, 1985). Using a technique known in the art, a transfer vector containing MAPP is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses MAPP is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from Trichoplusia ni (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately 2–5$\times10^5$ cells to a density of 1–2$\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the MAPP polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in Saccharomyces cerevisiae is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349.

Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. The use of *Pichia methanolica* as host for the production of recombinant proteins is disclosed in U.S. Pat. Nos. 5,716,808, 5,736,383, 5,854,039, and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a MAPP polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus oocytes* by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for MAPP amino acid residues.

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant MAPP proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, N.Y., 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

The polypeptides of the present invention can be isolated by a combination of procedures including, but not limited to, anion and cation exchange chromatography, size exclusion, and affinity chromatography. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

MAPP polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, Chem. Pept. Prot. 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, MAPP proteins can be prepared as monomers or multimers; glycosylated or nonglycosylated; pegylated or non-pegylated; and may or may not include an initial methionine amino acid residue.

The disintegrin loop (residue 475 to residue 488 of SEQ ID NO:2) is of particular interest for use in assays and treatment of disorders of the spinal cord, heart, aorta, colon, bladder, small intestine, uterus, prostate, stomach, testis, ovary, mammary gland, appendix, lung, trachea, fetal lung, and placenta. For these purposes the disintegrin loop peptide synthesis includes the terminal cysteine residues and thus, would be from residue 475 to residue 488 of SEQ ID NO:2. This peptide can be synthesized as a linear peptide or a disulfide linked peptide. Peptides having disulfide bonds between residues can be 475, 482, and 488 are of particular interest. See Jia, L. G., ibid for additional description of peptide synthesis and disulfide linkages.

The activity of MAPP polypeptides can be measured using a variety of assays that measure, for example, cell-cell interactions; proteolysis; extracellular matrix formation or remodeling; metastasis, and other biological functions associated with disintegrin family members or with integrin/disintegrin interactions, such as, apoptosis; or differentiation, for example. Of particular interest is a change in platelet aggregation. Assays measuring platelet aggregation are well known in the art. For a general reference, see Dennis, *PNAS* 87: 2471–2475, 1989.

Proteins, including alternatively spliced peptides, of the present invention are useful for tumor suppression, gamete maturation, immunologic recognition, and growth and differentiation either working in isolation, or in conjunction with other molecules (growth factors, cytokines, etc.) spinal cord, heart, aorta, colon, bladder, small intestine, uterus, prostate, stomach, testis, ovary, mammary gland, appendix, lung, trachea, fetal lung, and placenta. Alternative splicing of MAPP may cell-type specific and confer activity to specific tissues.

Another assay of interest measures or detects changes in proliferation, differentiation, development and/or and electrical coupling of muscle cells or myocytes. Additionally, the effects of a MAPP polypeptides on cell-cell interactions of fibroblasts, myoblasts, nerve cells, white blood cells, immune cells, gamete cells or cells, in general, of a reproductive nature, and tumor cells would be of interest to measure. Yet other assays examines changes in protease activity and apoptosis.

The activity of molecules of the present invention can be measured using a variety of assays that, for example, measure neogenesis or hyperplasia (i.e., proliferation) of cardiac cells based on the tissue specificity in adult heart. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured using cultured cardiac cells or in vivo by administering molecules of the claimed invention to an appropriate animal model. Generally, proliferative effects are observed as an increase in cell number and therefore, may include inhibition of apoptosis, as well as mitogenesis. Cultured cells include cardiac fibroblasts, cardiac myocytes, skeletal myocytes, human umbilical vein endothelial cells from primary cultures. Established cell lines include: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992) and LNCap.FGC adenocarcinoma cells (ATCC No. CRL-1740). Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabelled nucleotides (Cook et al., *Analytical Biochem.* 179:1–7, 1989), incorporation of 5-bromo-2' -deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

To determine if MAPP is a chemotractant in vivo, MAPP can be given by intradermal or intraperitoneal injection. Characterization of the accumulated leukocytes at the site of injection can be determined using lineage specific cell surface markers and fluorescence immunocytometry or by immunohistochemistry (Jose, *J. Exp. Med.* 179:881–87, 1994). Release of specific leukocyte cell populations from bone marrow into peripheral blood can also be measured after MAPP injection.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors and receptor-like complementary molecules. The stage of a cell population's differentiation is monitored by identification of markers present in the cell population. For example, myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. The novel polypeptides of the present invention are useful for studies to isolate mesenchymal stem cells and cardiac myocyte progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, MAPP polypeptides may stimulate inhibition or proliferation of endocrine and exocrine cells of the testes, ovary, prostate, small intestine, colon, spinal cord, heart, aorta, bladder, uterus, stomach, mammary gland, appendix, lung, trachea, fetal lung, and placenta.

Molecules of the present invention may, while stimulating proliferation or differentiation of cardiac myocytes, inhibit proliferation or differentiation of adipocytes, by virtue of their effect on common precursor/stem cells. The novel polypeptides of the present invention are useful to study neural and epithelial stem cells and testes, ovary, prostate, small intestine, colon, spinal cord, heart, aorta, bladder, uterus, stomach, mammary gland, appendix, lung, trachea, fetal lung, and placenta progenitor cells, both in vivo and ex vivo.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989).0

The MAPP polypeptides of the present invention can be used to study proliferation or differentiation in testes, ovary, prostate, small intestine, colon, spinal cord, heart, aorta, bladder, uterus, stomach, mammary gland, appendix, lung, trachea, fetal lung, and placenta. Such methods of the present invention generally comprise incubating cells derived from these tissues in the presence and absence of MAPP polypeptide, monoclonal antibody, agonist or antagonist thereof and observing changes in cell proliferation or differentiation. Cell lines from these tissues are commercially available from, for example, American Type Culture Collection (Manasas, Va.).

Proteins, including alternatively spliced peptides, and fragments, of the present invention are useful for studying cell-cell interactions, fertilization, development, immune recognition, growth control, tumor suppression, and gamete maturation. MAPP molecules, variants, and fragments can be applied in isolation, or in conjunction with other molecules (growth factors, cytokines, etc.) in testes, ovary, prostate, small intestine, colon, spinal cord, heart, aorta, bladder, uterus, stomach, mammary gland, appendix, lung, trachea, fetal lung, and placenta.

Proteins of the present invention are useful for delivery of therapeutic agents such as, but not limited to, proteases, radionuclides, chemotherapy agents, and small molecules. Effects of these therapeutic agents can be measured in vitro using cultured cells, ex vivo on tissue slices, or in vivo by administering molecules of the claimed invention to the appropriate animal model. An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated.

Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

As a soluble or cell-surface protein, the activity of MAPP polypeptide or a peptide to which MAPP binds, can be measured by a silicon-based biosensor microphysiometer which measures the extracellular acidification rate or proton excretion associated with cell-surface protein interactions and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including MAPP proteins, their, agonists, and antagonists. Preferably, the microphysiometer is used to measure responses of a MAPP-responsive eukaryotic cell, compared to a control eukaryotic cell that does not respond to MAPP polypeptide. MAPP-responsive eukaryotic cells comprise cells into which a polynucleotide for MAPP has been transfected creating a cell that is responsive to MAPP; or cells naturally responsive to MAPP. Differences, measured by a change in the response of cells exposed to MAPP polypeptide, relative to a control not exposed to MAPP, are a direct measurement of MAPP-modulated cellular responses. Moreover, such MAPP-modulated responses can be assayed under a variety of stimuli. The present invention provides a method of identifying agonists and antagonists of MAPP protein, comprising providing cells responsive to a MAPP polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of MAPP polypeptide and the absence of a test compound provides a positive control for the MAPP-responsive cells, and a control to compare the agonist activity of a test compound with that of the MAPP polypeptide. Antagonists of MAPP can be identified by exposing the cells to MAPP protein in the presence and absence of the test compound, whereby a reduction in MAPP-stimulated activity is indicative of agonist activity in the test compound.

Moreover, MAPP can be used to identify cells, tissues, or cell lines which respond to a MAPP-stimulated pathway. The microphysiometer, described above, can be used to rapidly identify disintegrin-responsive cells, such as cells responsive to MAPP of the present invention. Cells can be cultured in the presence or absence of MAPP polypeptide. Those cells which elicit a measurable change in extracellular acidification in the presence of MAPP are responsive to MAPP. Such cell lines, can be used to identify integrins, antagonists and agonists of MAPP polypeptide as described above. Using similar methods, cells expressing MAPP can be used to identify cells which stimulate a MAPP-signaling pathway.

In view of the tissue distribution (testes, ovary, prostate, small intestine, colon, spinal cord, heart, aorta, bladder, uterus, stomach, mammary gland, appendix, lung, trachea, fetal lung, and placenta) observed for MAPP expression, agonists (including the native disintegrin and protease domains, as well as a native or synthetic disintegrin loop peptide) and antagonists have enormous potential in both in vitro and in vivo applications. Compounds identified as MAPP agonists and antagonists are useful for studying cell-cell interactions, myogenesis, apoptosis, neurogenesis, tumor proliferation and suppression, extracellular matrix proteins, repair and remodeling of ischemia reperfusion and inflammation in vitro and in vivo. For example, MAPP and agonist compounds are useful as components of defined cell culture media, and may be used alone or in combination with other cytokines and hormones to replace serum that is commonly used in cell culture. Agonists are thus useful in specifically promoting the growth and/or development of cells of the myeloid and lymphoid lineages in culture. Additionally, MAPP polypeptides and MAPP agonists, including small molecules are useful as a research reagent, such as for the expansion, differentiation, and/or cell-cell interactions of testes, ovary, prostate, small intestine, colon, spinal cord, heart, aorta, bladder, uterus, stomach, mammary gland, appendix, lung, trachea, fetal lung, and placenta. MAPP polypeptides are added to tissue culture media for these cell types.

Antagonists are also useful as research reagents for characterizing sites of interactions between members of complement/anti-complement pairs as well as sites of cell-cell interactions. Inhibitors of MAPP activity (MAPP antagonists) include anti-MAPP antibodies and soluble MAPP polypeptides (such as in SEQ ID NO:2), as well as other peptidic and non-peptidic agents (including ribozymes).

MAPP can also be used to identify inhibitors (antagonists) of its activity. Test compounds are added to the assays disclosed herein to identify compounds that inhibit the activity of MAPP. In addition to those assays disclosed herein, samples can be tested for inhibition of MAPP activity within a variety of assays designed to measure disintegrin/integrin binding or the stimulation/inhibition of MAPP-dependent cellular responses. For example, MAPP-responsive cell lines can be transfected with a reporter gene construct that is responsive to a MAPP-stimulated cellular pathway. Reporter gene constructs of this type are known in the art, and will generally comprise a DNA response element operably linked to a gene encoding an assayable protein, such as luciferase, or a metabolite, such as cyclic AMP. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. The most likely reporter gene construct would contain a disintegrin that, upon binding an integrin, would signal intracellularly through, for example, a SRE reporter. Candidate compounds, solutions, mixtures or extracts are tested for the ability to inhibit the activity of MAPP on the target cells, as evidenced by a decrease in MAPP stimulation of reporter gene expression. Assays of this type will detect compounds that directly block MAPP binding to a cell-surface protein, i.e., integrin, or the anti-complementary member of a complementary/anti-complementary pair, as well as compounds that block processes in the cellular pathway subsequent to complement/anti-complement binding. In the alternative, compounds or other samples can be tested for direct blocking of MAPP binding to a integrin using MAPP tagged with a detectable label (e.g., $^{125}I$ , biotin, horseradish peroxidase, FITC, and the like). Within assays of this type, the ability of a test sample to inhibit the binding of labeled MAPP to the integrin is indicative of inhibitory activity, which can be confirmed through secondary assays. Integrins used within binding assays may be cellular integrins, soluble integrins, or isolated, immobilized integrins.

The amino acid sequence comprising the DCD integrin binding component of MAPP, (residues 481 to 483 of SEQ ID NO:2), which is analogous to the "RGD", integrin binding loop, may also be used as an inhibitor. Such an inhibitor would bind an integrin other than its naturally occurring integrin by nature of its folding structure. Particular interests in such an inhibitor would be to mediate platelet aggregation, gamete maturation, or immunologic response. Assays measuring binding and inhibition are known in the art.

Also, MAPP polypeptides, agonists or antagonists thereof may be therapeutically useful for promoting wound healing, for example, in testes, ovary, prostate, small intestine, colon, spinal cord, heart, aorta, bladder, uterus, stomach, mammary gland, appendix, lung, trachea, fetal lung, and placenta tissues. To verify the presence of this capability in MAPP polypeptides, agonists or antagonists of the present invention, such MAPP polypeptides, agonists or antagonists are evaluated with respect to their ability to facilitate wound healing according to procedures known in the art. If desired, MAPP polypeptide performance in this regard can be compared to growth factors, such as EGF, NGF, TGF-α, TGF-β, insulin, IGF-I, IGF-II, fibroblast growth factor (FGF) and the like. In addition, MAPP polypeptides or agonists or antagonists thereof may be evaluated in combination with one or more growth factors to identify synergistic effects.

A MAPP ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing integrins are passed through the column one or more times to allow integrins to bind to the integrin binding loop polypeptide. The integrin is then eluted using changes in salt concentration, chaotropic agents (guanidine HCl), or pH to disrupt integrin, or receptor binding.

An assay system that uses a ligand-binding receptor (or an antibody, one member of a complementary/anti-complementary pairor other cell-surface binding protein) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member, disintegrin or fragment is covalently attached, using amine or sulfhydryl chemistry, to dextran fibers that are attached to gold film within the flow cell. A test sample is passed through the cell. If an integrin, epitope, or opposite member of the complementary/anti-complementary pair is present in the sample, it will bind to the immobilized disintegrin, antibody or member, respectively, causing a change in the refractive index of the medium, which is detected as a change in surface plasmon resonance of the gold film. This system allows the determination of on- and off-rates, from which binding affinity can be calculated, and assessment of.

Integrin polypeptides and other receptor polypeptides which bind disintegrin polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

A "soluble protein" is a protein that is not bound to a cell membrane. Soluble proteins are most commonly ligand-binding receptor polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively.

Soluble forms of MAPP polypeptides, such as the polypeptide of SEQ ID NOs:2, may act as antagonsits to or agonists of MAPP polypeptides, and would be useful to modulate the effects of MAPP in testes, ovary, prostate, small intestine, colon, spinal cord, heart, aorta, bladder, uterus, stomach, mammary gland, appendix, lung, trachea, fetal lung, and placenta. Thus, the isoform of MAPP that does not contain a transmembrane domain (i.e., the polypeptides of SEQ ID NO:2) will be soluble, and may act as an agonist or antagonist of MAPP activity. Since polypeptides of this nature are not anchored to the membrane, they can act at sites distant from the tissues in which they are expressed. Thus, the activity of the soluble form of MAPP polypeptides can be more wide spread than its membrane-anchored counterpart. Both isoforms would be useful in studying the effects of the present invention in vitro an in vivo.

Molecules of the present invention can be used to identify and isolate integrins, or members of complement/anti-complement pairs involved in cell-cell interactions. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The molecules of the present invention will be useful in repair and remodeling after an ischemic event, modulating immunologic recognition, gamete maturation, and/or platelet aggregation. The polypeptides, nucleic acid and/or antibodies of the present invention can be used in treatment of disorders associated with infarct in brain or heart tissue, and/or platelet aggregation. The molecules of the present invention can be used to modulate proteolysis, apoptosis, neurogenesis, myogenesis, cell adhesion, cell fusion, and signaling or to treat or prevent development of pathological conditions in such diverse tissue as testes, ovary, prostate, small intestine, colon, spinal cord, heart, aorta, bladder, uterus, stomach, mammary gland, appendix, lung, trachea, fetal lung, and placenta. In particular, certain diseases may be amenable to such diagnosis, treatment or prevention. The molecules of the present invention can be used to modulate inhibition and proliferation of neurons and myocytes in testes, ovary, prostate, small intestine, colon, spinal cord, heart, aorta, bladder, uterus, stomach, mammary gland, appendix, lung, trachea, fetal lung, and placenta. Disorders which may be amenable to diagnosis, treatment or prevention with MAPP polypeptides include, for example, Alzheimers's Disease, tumor formation, Multiple Sclerosis, Congestive Heart Failure, Ischemic Reperfusion or infarct, and degenerative diseases.

Additionally, the propeptide domain, comprising residues 31 to 200, can be used as a modulator of protease activity of other DP family members as well as other proteases, in general. Polypeptides and polynucleotides encoding them can be used as a soluble molecule or as a fusion product to regulate such proteases.

Polynucleotides encoding MAPP polypeptides are useful within gene therapy applications where it is desired to increase or inhibit MAPP activity. If a mammal has a mutated or absent MAPP gene, the MAPP gene can be introduced into the cells of the mammal. In one embodiment, a gene encoding a MAPP polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a MAPP gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Similarly, the MAPP polynucleotides (SEQ ID NO:1 or SEQ ID NO:3) can be used to target specific tissues such as testes, ovary, prostate, small intestine, colon, spinal cord, heart, aorta, bladder, uterus, stomach, mammary gland, appendix, lung, trachea, fetal lung, and placenta. It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Various techniques, including antisense and ribozyme methodologies, can be used to inhibit MAPP gene transcription and translation, such as to inhibit cell proliferation in vivo. Polynucleotides that are complementary to a segment of a MAPP-encoding polynucleotide (e.g., a polynucleotide as set forth in SEQ ID NOs:1 or 3) are designed to bind to MAPP-encoding mRNA and to inhibit translation of such mRNA. Such antisense polynucleotides are used to inhibit expression of MAPP polypeptide-encoding genes in cell culture or in a subject.

Mice engineered to express the MAPP gene, referred to as "transgenic mice," and mice that exhibit a complete absence of MAPP gene function, referred to as "knockout mice," may also be generated (Snouwaert et al., *Science* 257:1083, 1992), may also be generated (Lowell et al., *Nature* 366:740–42, 1993; Capecchi, M. R., *Science* 244:1288–1292, 1989; Palmiter, R. D. et al. *Annu Rev Genet.* 20:465–499, 1986). For example, transgenic mice that over-express MAPP, either ubiquitously or under a tissue-specific or tissue-restricted promoter can be used to ask whether over-expression causes a phenotype. For example, over-expression of a wild-type MAPP polypeptide, polypeptide fragment or a mutant thereof may alter normal cellular processes, resulting in a phenotype that identifies a tissue in which MAPP expression is functionally relevant and may indicate a therapeutic target for the MAPP, its agonists or antagonists. For example, a preferred transgenic mouse to engineer is one that over-expresses the soluble MAPP polypeptide (approximately amino acids 28 to 802 of SEQ ID NO:2). Moreover, such over-expression may result in a phenotype that shows similarity with human diseases. Similarly, knockout MAPP mice can be used to determine where MAPP is absolutely required in vivo. The phenotype of knockout mice is predictive of the in vivo effects of that a MAPP antagonist, such as those described herein, may have. The human MAPP cDNA can be used to isolate murine MAPP mRNA, cDNA and genomic DNA, which are subsequently used to generate knockout mice. These mice may be employed to study the MAPP gene and the protein encoded thereby in an in vivo system, and can be used as in vivo models for corresponding human diseases. Moreover, transgenic mice expression of MAPP antisense polynucleotides or ribozymes directed against MAPP, described herein, can be used analogously to transgenic mice described above.

MAPP polypeptides, variants, and fragments thereof, may be useful as replacement therapy for disorders associated with cell-cell interactions, including disorders related to, for example, fertility, gamete maturation, immunology, coagulation, trauma, and epithelial disorders, in general.

A less widely appreciated determinant of tissue morphogenesis is the process of cell rearrangement: Both cell motility and cell-cell adhesion are likely to play central roles in morphogenetic cell rearrangements. Cells need to be able to rapidly break and probably simultaneously remake contacts with neighboring cells. See Gumbiner, B. M., *Cell* 69:385–387, 1992. As a secreted protein in testes, ovary, prostate, small intestine, colon, spinal cord, heart, aorta, bladder, uterus, stomach, mammary gland, appendix, lung, trachea, fetal lung, and placenta, MAPP can play a role in intercellular rearrangement in these and other tissues.

MAPP gene may be useful to as a probe to identify humans who have a defective MAPP gene. The strong expression of MAPP in testes, ovary, prostate, small intestine, colon, spinal cord, heart, aorta, bladder, uterus, stomach, mammary gland, appendix, lung, trachea, fetal lung, and placenta suggests that MAPP polynucleotides or polypeptides can be used as measured as an indication of aberrant growth in these tissues. Thus, polynucleotides and polypeptides of MAPP, and mutations to them, can be used a diagnostic indicators of cancer in these tissues.

The polypeptides of the present invention are useful in studying cell adhesion and the role thereof in metastasis and may be useful in preventing metastasis, in particular metastasis in tumors of the testes, ovary, prostate, small intestine, colon, spinal cord, heart, aorta, bladder, uterus, stomach, mammary gland, appendix, lung, trachea, fetal lung, and placenta. Similarly, polynucleotides and polypeptides of MAPP may be used to replace their defective counterparts in tumor or malignant tissues.

The MAPP polypeptide is expressed in the testes, ovary, prostate, small intestine, colon, spinal cord, heart, aorta, bladder, uterus, stomach, mammary gland, appendix, lung, trachea, fetal lung, and placenta. Thus, MAPP polypeptide pharmaceutical compositions of the present invention may be useful in prevention or treatment of disorders associated with pathological regulation or the expansion of testes, ovary, prostate, small intestine, colon, spinal cord, heart, aorta, bladder, uterus, stomach, mammary gland, appendix, lung, trachea, fetal lung, and placenta.

In consideration of the strong expression of MAPP in testes, prostate and ovary and the similarity of the disintegrin loop of MAPP (i.e, residues 475 to 488 of SEQ ID NO:2) to that of fertilin suggest a role in reproduction for MAPP polypeptides and polynucleotides. Thus MAPP can be used to study sperm-egg fusion in vitro. Such assays are described, for example, by Myles, D. G., et al., (*PNAS* 91: 4195–4198, 199, and Almeida, E. A., et al., (*Cell* 81: 1095–1104, 1995).

The polynucleotides of the present invention may also be used in conjunction with a regulatable promoter, thus allowing the dosage of delivered protein to be regulated.

The MAPP polynucleotides of SEQ ID NO:2 have been mapped to chromosome 20p13. Thus, the present invention also provides reagents which will find use in diagnostic applications. For example, the MAPP gene, a probe comprising MAPP DNA or RNA or a subsequence thereof can be used to determine if the MAPP gene is present on chromosome 20p13 or if a mutation has occurred. Detectable chromosomal aberrations at the MAPP gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibi.; Marian, *Chest* 108:255–65, 1995).

The MAPP gene is localized to chromosome 20, at 20p13. One of the syndromes that have been localized to this region is Alagille Syndrome, (OMIM entry #118450) which is characterized by pulmonic valvular stenosis and peripheral arterial stenosis in the heart. Other syndromes which map to this region include Corneal Endothelial Dystrophy 1 and 2 (OMIM entry 121700, and 21770, respectively), which result in vision impairment and corneal clouding; Noncompaction of Left Ventricular Myocardium (OMIM entry 604169), which is a heart malformation (“spongy myocardium”); and Hallervorden-Spatz Disease (OMIM entry 234200, also known as Neurodegeneration with Brain Iron Accumulation), which characterized by general dystonia, oromandibular involvement, behavioral changes followed by dementia, and visual impairment due to retinal degeneration and/or bilateral optic atrophy. Thus, the identification and mapping of this region of chromosome 20 is needed to study these diseases in greater detail. MAPP polynucleotides or fragments thereof, may be used to identify this region (20p13) of chromosome 20.

For pharmaceutical use, the proteins of the present invention can be administered orally, rectally, parenterally (particularly intravenous or subcutaneous), intracistemally, intravaginally, intraperitoneally, topically (as powders, ointments, drops or transdermal patch) bucally, or as a pulmonary or nasal inhalant. Intravenous administration will be by bolus injection or infusion over a typical period of one to several hours. In general, pharmaceutical formulations will include a MAPP protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 $\mu$g/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of MAPP is an amount sufficient to produce a clinically significant change in extracellular matrix remodeling, scar tissue formation, tumor suppression, platelet aggregation, apoptosis, myogenesis, testes, ovary, prostate, small intestine, colon, spinal cord, heart, aorta, bladder, uterus, stomach, mammary gland, appendix, lung, trachea, fetal lung, and placenta tissues. Similarly, a therapeutically effective amount of MAPP is an amount sufficient to produce a clinically significant change in disorders associated with spinal cord, colon, prostate, stomach, ovary, pancreas, pituitary gland, adrenal gland, salivary gland, mammary gland, liver, small intestine, spleen, thymus, peripheral leukocyte, lymph node, bone marrow, lung, trachea, placenta, fetal spleen and fetal lung.

The invention is further illustrated by the following non-limiting examples.

EXAMPLES

From the foregoing, it will be appreciated that, although specific embodiments of the invention have been described herein for purposes of illustration, various modifications may be made without deviating from the spirit and scope of the invention. Accordingly, the invention is not limited except as by the appended claims.

Example 1

Extension of EST Sequence

The novel MAPP polypeptide-encoding polynucleotides of the present invention were initially identified by querying a database of partial sequences. This query identified a cDNA clone of which the insert was determined to be incomplete. A positive pool of 250 clones was identified by screening by polymerase chain reaction of an arrayed human pituitary cDNA plasmid library using primers ZC18,604 (SEQ ID NO:18), and ZC18,605 (SEQ ID NO:19) and the following thermocycler conditions: one cycle at 94° C. for 2 minutes; followed by thirty-five cycles at 94° C. for 10 seconds, 62° C. for 20 seconds, 72° C. for 30 seconds, followed by one cycle at 72° C. for 7 minutes, followed by a 4° C. hold. The positive pool of clones was electroporated into competent DH10B *E. coli* cells (Gibco BRL, Rockville, Md.) as per manufacturer’s directions. Colony lifts were performed with Hybond-N filters (Amersham, England) as per manufacturer's directions. Positive clones were identified by autoradiography: A 140 nucleotide probe corresponding to nucleotides 1847 to 1987 was generated by PCR using primers ZC17,993 (SEQ ID NO:7) and ZC17,994, (SEQ ID NO:8) and thermocycler conditions as above. The PCR fragment was gel purified (Qiagen II Gel Extraction Kit, Qiagen, Chatsworth, Calif.), radiolabeled (Rediprime II DNA Labelling System, Amersham, Piscataway, N.J.), and purified (NucTrap® Probe Purification Column, Stratagene, La Jolla, Calif.), all according to manufacturer's directions. The probe was hybridized to the filters at 55° C. overnight. Stringency and wash conditions were as follows: ExpressHyb Hybridization Solution (CLONTECH Laboratories, Inc., Palo Alto, Calif.) was used for prehybridization as well as hybridization. The filters were washed in 2×SSC and 0.1% SDS at room temperature, followed by a wash with the same concentrations of SSC and SDS, at 65° C., followed by a wash in 0.1×SSC and 0.1% SDS at 65° C. Autoradiographs were made of the filters, a positive clone was identified, and the plasmid was sequenced. Analysis of the sequence confirmed the sequence of the domains for the original partial sequence and extended the sequence to include nucleotides 639 to nucleotide 3431 of SEQ ID NO:1.

An additional pool of cDNA plasmids was identified by PCR from an arrayed human fetal brain library and primers ZC20,646 (SEQ ID NO:20) and ZC20,634 (SEQ ID NO:21), and thermocycler conditions as described above. The cDNA corresponding to the amino terminal of MAPP was amplified by RACE PCR using this positive pool of cDNA as template, primer ZC20,633 (SEQ ID NO:22), and a vector primer, ZC13,006 (SEQ ID NO:23). Thermocycler conditions were: one cycle at 94° C. for 2 minutes; followed by five cycles at 94° C. for 10 seconds, 68° C. for 2 minutes, followed by thirty-five cycles at 94° C. for 10 seconds, 62° C. for 20 seconds, 72° C. for 2 minutes, followed by one cycle at 72° C. for 7 minutes, followed by a 4° C. hold. The PCR fragment was gel purified, (Qiagen II Gel Extraction Kit, Qiagen, Los Angeles, Calif.) and the sequence of the PCR fragment confirmed the MAPP polynucleotide sequence and extended the amino terminal of the MAPP sequence. However, the sequence of the PCR fragment also contained intronic sequence.

An additional PCR was performed using newly designed internal primers, ZC21,076 (SEQ ID NO:24) and ZC20,633 (SEQ ID NO:25), human prostate cDNA (prepared with the Clontech Marathon cDNA protocol, CLONTECH Laboratories, Inc., Palo Alto, Calif.) as template, and the following thermolcycler conditions: one cycle at 94° C. for 2 minutes; five cycles at 94° C. for 15 seconds, 70° C. for 40 seconds, followed by thirty cycles at 94° C. for 15 seconds, 65° C. for 20 seconds, 72° C. for 40 seconds, followed by one cycle at 72° C. for 7 minutes, followed by a 4° C. hold. The PCR fragment was gel purified and sequenced as above. The intron was elimated and the, MAPP polynucleotide sequence was extended in the amino terminal to nucleotide 80 of SEQ ID NO:2.

Further elucidation of the amino terminal of the sequence was determined by PCR using human prostate Marathon® cDNA (CLONTECH Laboratories, Inc., Palo Alto, Calif.), with an internal primer, ZC21,074 (SEQ ID NO:26) and a primer provided with the Marathon® cDNA, API (SEQ ID NO:9). Thermocycler conditions were as follows: one cycle at 94° C. for 2 minutes; five cycles at 94° C. for 15 seconds, 70° C. for 45 seconds, followed by thirty cycles at 94° C. for 15 seconds, 65° C. for 20 seconds, 72° C. for 45 seconds, followed by one cycle at 72° C. for 7 minutes, followed by a 4° C. hold A dilution of this PCR product was used as template in a "nested" PCR wherein a new internal primer, ZC21,075 (SEQ ID NO:27) and another primer provided with the Marathon® cDNA, APII (SEQ ID NO:10), were used. Thermocycler conditions were: one cycle at 94° C. for 2 minutes; five cycles at 94° C. for 15 seconds, 74° C. for 30 seconds, followed by five cycles at 94° C. for 15 seconds, 70° C. for 30 seconds, followed by fifteen cycles at 94° C. for 15 seconds, 66° C. for 30 seconds, 72° C. for 30 seconds, followed by one cycle at 72° C. for 7 minutes, followed by a 4° C. hold. The reaction products were electrophoresed and the major product was gel extracted using the Qiagen II Gel Extraction Kit. The PCR fragment was subcloned into a commercially available vector, pCR2.1 (Invitrogen, Carlsbad, Calif.). Positive clones were sequenced resulting in further elucidation of the amino terminal of the MAPP polynucleotide sequence. Thus the final polynucleotide sequence of this variant of MAPP is shown in SEQ ID NO:1. The translated polypeptide sequence is shown in SEQ ID NO:2.

Since alternatively spliced isoforms of members of the DP family of proteins are known to exist, an additional PCR was performed using primers ZC17,994 (SEQ ID NO:8) and ZC18,262 (SEQ ID NO:11) to identify another variant of MAPP. Human spinal cord Marathon® cDNA (CLONTECH Laboratories, Inc., Palo Alto, Calif.) was used as template. The resulting PCR product was gel purified and sequenced as above. Sequence analysis showed a variant form of MAPP. The polynucleotide sequence for this clone is shown in SEQ ID NO:3, and the polypeptide sequence is shown in SEQ ID NO:4.

Example 2

Tissue Distribution

Analysis of tissue distribution was performed by the Northern blotting technique using Human Multiple Tissue and Master Dot Blots (CLONTECH Laboratories, Inc., Palo Alto, Calif.). Probe generation, hybridization and wash stringencies were similar to that described in Example 1. Strong signals of a single transcript of ~4.4 kb was seen in prostate, testis, ovary, small intestine, and colon with fainter signals in stomach, thyroid, spinal cord, lymph node, and trachea. Two transcript sizes of medium intensity were seen in heart at ~4.0 kb and ~4.4 kb. The Master Dot Blot contained RNA from various tissues that were normalized to 8 housekeeping genes was also probed and hybridized as described above. Low level expression was seen in all tissues on the Master Dot Blot with high level expression in spinal cord, heart, aorta, colon, bladder, uterus, prostate, stomach, testis, ovary, mammary gland, appendix, lung, trachea, fetal lung, and placenta.

Example 3

Protein Purification

Purification conditions for MAPP with N- and C-terminal EE tags:

*E. coli*, Pichia, CHO and BHK cells are transfected with expression vectors containing the DNA sequence of SEQ ID NO:1, or a portion thereof, operably linked to a polynucleotide encoding a Glu-Glu tag. MAPP protein is expressed in conditioned media of *E. coli, Pichia methanolica*, and or chinese hamster ovary (CHO) and MAPP protein is expressed in the conditioned media. For MAPP expressed in *E. coli* and Pichia, the media is not concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then concentrated to about 1.3 liters using a Millipore ProFlux A30 tangential flow concentrator fitted with a 3000 kDa cutoff Amicon (Bedford, Mass.) S1OY3 membrane. The concentrated material is again sterile-filtered with the Gelman filter, as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 50.0 ml sample of anti-EE Sepharose, prepared as described below, is added and the mixture gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.), and the gel is washed with 30 column volumes of phosphate buffered saline (PBS). The unretained flow-through fraction is discarded. Once the absorbance of the effluent at 280 nM is less than 0.05, flow through the column is reduced to zero, and the anti-EE Sepharose gel is washed with 2.0 column volumes of PBS containing 0.2 mg/ml of EE peptide (AnaSpec, San Jose, Calif.). The peptide that is used has the sequence GluTyrMetProValAsp. After 1.0 h at 4° C., flow is resumed and the eluted protein collected. This fraction is referred to as the peptide elution. The anti-EE Sepharose gel is then washed with 2.0 column volumes of 0.1 M glycine, pH 2.5, and the glycine wash is collected separately. The pH of the glycine-eluted fraction is adjusted to 7.0 by the addition of a small volume of 10×PBS and stored at 4° C. for future analysis, if needed.

The peptide elution is concentrated to 5.0 ml using a 15,000 molecular weight cutoff membrane concentrator (Millipore, Bedford, Mass.), according to the manufacturer's instructions. The concentrated peptide elution is then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions are collected and the absorbance at 280 nM monitored. The first peak of material absorbing at 280 nM and eluting near the void volume of the column is collected. This fraction is pure MAPP NEE or MAPP CEE. The pure material is concentrated as described above, analyzed by SDS-PAGE and Western blotting with anti-EE antibodies, aliquoted, and stored at −80° C. according to standard procedures.

Preparation of Anti-EE Sepharose:

A 100 ml bed volume of protein G-Sepharose (Pharmacia, Piscataway, N.J.) is washed 3 times with 100 ml of PBS containing 0.02% sodium azide using a 500 ml Nalgene 0.45 micron filter unit. The gel is washed with 6.0 volumes of 200 mM triethanolamine, pH 8.2 (TEA, Sigma, St. Louis, Mo.). and an equal volume of EE antibody solution containing 900 mg of antibody is added. After an overnight incubation at 4° C., unbound antibody is removed by washing the resin with 5 volumes of 200 mM TEA as described above. The resin is resuspended in 2 volumes of TEA, transferred to a suitable container, and dimethylpimilimidate-2HCl (Pierce, Rockford, Ill., dissolved in TEA, is added to a final concentration of 36 mg/ml of gel. The gel is rocked at room temperature for 45 min and the liquid is removed using the filter unit as described above. Nonspecific sites on the gel are then blocked by incubating for 10 min at room temperature with 5 volumes of 20 mM ethanolamine in 200 mM TEA. The gel is then washed with volumes of PBS containing 0.02% sodium azide and stored in this solution at 4° C.

Purification of Untagged MAPP

*E. coli*, Pichia, CHO and BHK cells are transfected with expression vectors containing the DNA sequence of SEQ ID NO:1, or a portion thereof. The procedure described below is used for protein expressed in conditioned medium of *E. coli, Pichia methanolica*, and Chinese hamster ovary (CHO) and baby hamster kidney (BHK) cells. For MAPP expressed in *E. coli* and Pichia, however, the medium is not be concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) SOY3 membrane. The concentrated material is again be sterile-filtered with the Gelman filter as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim).

The procedures outlined below are adaptations of those used to purify metalloprotease/disintegrins from *Crotalus viridus* and *Crotalus atrox* venom (Liu et al., *Toxicol.* 33: 1289–1298, 1995; Shimokawa et al., *Arch Biochem Biophys* 343: 35–43, 1997). A combination of procedures including, but not limited to, anion and cation exchange chromatography, size exclusion, and affinity chromography is used to purify untagged MAPP.

Concentrated conditioned medium is diluted 1/10 in line with 10 mM borate buffer, pH 9.0, 0.1 M NaCl, and 2.0 mM $CaCl_2$ using the BioCad Sprint HPLC (PerSeptive BioSystems, Framingham, Mass.). The material is pumped onto a 3.5×20 cm Poros HQ (PerSeptive BioSystems, Framingham, Mass.) column at 5 ml/min. The column is washed with loading buffer, and when the absorbance of the effluent is less than 0.05, the column is developed with a linear gradient of NaCl from 0.1 M to 1.0 M NaCl. Fractions containing MAPP are identified by SDS-PAGE and Western blotting with anti-MAPP peptide antibodies. MAPP-containing fractions are pooled together, and concentrated using an Amicon stirred cell concentrator fitted with a YM-10 membrane. The Poros HQ pool is then chromatographed on a Sephadex G-75 column equilibrated in 10 mM sodium phosphate, pH 7.0. Fractions containing MAPP are identified and pooled together, as described above, and applied to a 1.0×5 cm Poros HA hydroxyapatite column at 1.0 ml/min using the BioCad Sprint HPLC. The column is washed with loading buffer and developed with a linear gradient from 10 mM to 500 mM sodium phosphate. Fractions contained pure MAPP are identified by SDS-PAGE and Western blotting, as described above. The purified material is aliquoted and stored as described above.

Example 4

Chromosomal Assignment of MAPP

MAPP was mapped to chromosome 20 using the commercially available version of the Stanford G3 Radiation Hybrid Mapping Panel (Research Genetics, Inc., Huntsville, Ala.). The Stanford G3 RH Panel contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers.

For the mapping of MAPP with the "Stanford G3 RH Panel", 20 μl reactions were set up in a PCRable 96-well microtiter plate (Stratagene, La Jolla, Calif.) and used in a RoboCycler Gradient 96 thermal cycler (Stratagene). Each of the 85 PCR reactions consisted of 2 μl 10× KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC 22,481 (SEQ ID NO:12), 1 μl antisense primer, ZC 22,482 (SEQ ID NO:13), 2 μl RediLoad (Research Genetics, Inc., Huntsville, Ala.), 0.4 μl 50× Advantage KlenTaq Polymerase Mix (CLONTECH Laboratories, Inc., Palo Alto, Calif.), 25 ng of DNA from an individual hybrid clone or control and ddH2O to make a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 70° C. and 1 minute AND 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of MAPP to the framework marker SHGC-11829 with a LOD score of >10 and at a distance of 7 cR_10000 from the marker. The use of surrounding markers positions MAPP in the 20p13 region on the integrated LDB chromosome 20 map (The Genetic Location Database, University of Southhampton, WWW server: http://cedar.genetics. soton.ac.uk/public__html/).

Example 5

Synthesis of Peptides

A peptide corresponding to amino acid residue 475 (Cys) to amino acid residue 488 (Cys) of SEQ ID NO:2, is synthesized by solid phase peptide synthesis using a model 431A Peptide Synthesizer (Applied Biosystems/Perkin Elmer, Foster City, Calif.). Fmoc-Glutamine resin (0.63 mmol/g; Advanced Chemtech, Louisville, Ky.) is used as the initial support resin. 1 mmol amino acid cartridges (Anaspec, Inc. San Jose, Calif.) are used for synthesis. A mixture of 2(1-Hbenzotriazol-y-yl 1,1,3,3-tetrahmethylhyluronium hexafluorophosphate (HBTU), 1-hydroxybenzotriazol (HOBt), 2 m N,N-Diisolpropylethylamine, N-Methylpyrrolidone, Dichloromethane (all from Applied Biosystems/Perkin Elmer) and piperidine (Aldrich Chemical Co., St. Louis, Mo.), are used for synthesis reagents.

The Peptide Companion software (Peptides International, Louisville, Ky.) is used to predict the aggregation potential and difficulty level for synthesis for the zdint-1 peptide. Synthesis is performed using single coupling programs, according to the manufacturer's specifications.

The peptide is cleaved from the solid phase following standard TFA cleavage procedure (according to Peptide Cleavage manual, Applied Biosystems/Perkin Elmer). Purification of the peptide is done by RP-HPLC using a C18, 10 μm semi-peparative column (Vydac, Hesperial, Calif.). Eluted fractions from the column are collected and analyzed for correct mass and purity by electrospray mass spectrometry. Pools of the eluted material are collected. If pure, the pools are combined, frozen and lyophilized.

Example 6

Anticoagulant Activity of MAPP

The ability of the MAPP protein to inhibit clotting is measured in a one-stage clotting assay using wild-type MAPP as a control. Recombinant proteins are prepared essentially as described above from cells cultured in media containing 5mg/ml vitamin K. Varying amounts of the MAPP or recombinant wild-type MAPP are diluted in 50 mM Tris pH 7.5, 0.1% BSA to 100 ml. The mixtures are incubated with 100 ml of MAPP-deficient plasma and 200 ml of thromboplastin C (Dade, Miami, Fla.; contains rabbit brain thromboplastin and 11.8 mM $Ca^{++}$). The clotting assay is performed in an automatic coagulation timer (MLA Electra 800, Medical Laboratory Automation Inc., Pleasantville, N.Y.), and clotting times are converted to units of MAPP activity using a standard curve constructed with 1:5 to 1:640 dilutions of normal pooled human plasma (assumed to contain one unit per ml MAPP activity; prepared by pooling citrated serum from healthy donors).

MAPP activity is seen as a reduction in clotting time over control samples.

Example 7

Inhibition of Platelet Accumulation with MAPP

MAPP is analyzed for its ability to inhibit platelet accumulation at sites of arterial thrombosis due to mechanical injury in non-human primates. A model of aortic endarterectomy is utilized in baboons, essentially as described by Lumsden et al. (Blood 81: 1762–1770 (1993)). A section of baboon aorta 1–2 cm in length is removed, inverted and scraped to remove the intima of the artery and approximately 50% of the media. The artery is reverted back to its correct orientation, cannulated on both ends and placed into an extracorporeal shunt in a baboon, thereby exposing the mechanically injured artery to baboon blood via the shunt. Just prior to opening of the shunt to the circulating blood, $^{111}$In-labeled autologous platelets are injected intravenously into the animal. The level of platelet accumulation at the site of the injured artery is determined by real-time gamma camera imaging.

Evaluation of MAPP for inhibition of platelet accumulation is done using bolus injections of MAPP or saline control and are given just prior to the opening of the shunt. The injured arteries are measured continuously for 60 minutes.

MAPP activity is seen as an inhibition of platelet accumulation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide molecule comprising residues 1 to 802 of SEQ ID NO:2.

2. An isolated polypeptide molecule comprising residues 1 to 812 of SEQ ID NO:4.

* * * * *

SEQUENCE LISTING

```
<160> NUMBER OF SEQ ID NOS:  26

<210> SEQ ID NO 1
<211> LENGTH: 3431
<212> TYPE: DNA
<213> ORGANISM: Homo sapiens
<220> FEATURE:
<221> NAME/KEY: CDS
<222> LOCATION: (37)...(2442)

<400> SEQUENCE: 1

gcgagccgct gcctagaggc cgaggagctc acagct atg ggc tgg agg ccc cgg       54
                                        Met Gly Trp Arg Pro Arg
                                         1               5

aga gct cgg ggg acc ccg ttg ctg ctg cta cta ctg ctg ctg ctc      102
Arg Ala Arg Gly Thr Pro Leu Leu Leu Leu Leu Leu Leu Leu Leu
             10                  15                  20

tgg cca gtg cca ggc gcc ggg gtg ctt caa gga cat atc cct ggg cag      150
Trp Pro Val Pro Gly Ala Gly Val Leu Gln Gly His Ile Pro Gly Gln
         25                  30                  35

cca gtc acc ccg cac tgg gtc ctg gat gga caa ccc tgg cgc acc gtc      198
Pro Val Thr Pro His Trp Val Leu Asp Gly Gln Pro Trp Arg Thr Val
     40                  45                  50

agc ctg gag gag ccg gtc tcg aag cca gac atg ggg ctg gtg gcc ctg      246
Ser Leu Glu Glu Pro Val Ser Lys Pro Asp Met Gly Leu Val Ala Leu
 55                  60                  65                  70

gag gct gaa ggc cag gag ctc ctg ctt gag ctg gag aag aac cac agg      294
Glu Ala Glu Gly Gln Glu Leu Leu Leu Glu Leu Glu Lys Asn His Arg
                 75                  80                  85

ctg ctg gcc cca gga tac ata gaa acc cac tac ggc cca gat ggg cag      342
Leu Leu Ala Pro Gly Tyr Ile Glu Thr His Tyr Gly Pro Asp Gly Gln
             90                  95                 100

cca gtg gtg ctg gcc ccc aac cac acg gat cat tgc cac tac caa ggg      390
Pro Val Val Leu Ala Pro Asn His Thr Asp His Cys His Tyr Gln Gly
        105                 110                 115

cga gta agg ggc ttc ccc gac tcc tgg gta gtc ctc tgc acc tgc tct      438
Arg Val Arg Gly Phe Pro Asp Ser Trp Val Val Leu Cys Thr Cys Ser
    120                 125                 130

ggg atg agt ggc ctg atc acc ctc agc agg aat gcc agc tat tat ctg      486
Gly Met Ser Gly Leu Ile Thr Leu Ser Arg Asn Ala Ser Tyr Tyr Leu
135                 140                 145                 150

cgt ccc tgg cca ccc cgg ggc tcc aag gac ttc tca acc cac gag atc      534
Arg Pro Trp Pro Pro Arg Gly Ser Lys Asp Phe Ser Thr His Glu Ile
                155                 160                 165

ttt cgg atg gag cag ctg ctc acc tgg aaa gga acc tgt ggc cac agg      582
Phe Arg Met Glu Gln Leu Leu Thr Trp Lys Gly Thr Cys Gly His Arg
            170                 175                 180

gat cct ggg aac aaa gcg ggc atg acc agc ctt cct ggt ggt ccc cag      630
Asp Pro Gly Asn Lys Ala Gly Met Thr Ser Leu Pro Gly Gly Pro Gln
        185                 190                 195

agc agg ggc agg cga gaa gcg cgc agg acc cgg aag tac ctg gaa ctg      678
Ser Arg Gly Arg Arg Glu Ala Arg Arg Thr Arg Lys Tyr Leu Glu Leu
    200                 205                 210

tac att gtg gca gac cac acc ctg ttc ttg act cgg cac cga aac ttg      726
Tyr Ile Val Ala Asp His Thr Leu Phe Leu Thr Arg His Arg Asn Leu
215                 220                 225                 230

aac cac acc aaa cag cgt ctc ctg gaa gtc gcc aac tac gtg gac cag      774
Asn His Thr Lys Gln Arg Leu Leu Glu Val Ala Asn Tyr Val Asp Gln
                235                 240                 245
```

-continued

```
ctt ctc agg act ctg gac att cag gtg gcg ctg acc ggc ctg gag gtg       822
Leu Leu Arg Thr Leu Asp Ile Gln Val Ala Leu Thr Gly Leu Glu Val
            250                 255                 260

tgg acc gag cgg gac cgc agc cgc gtc acg cag gac gcc aac gcc acg       870
Trp Thr Glu Arg Asp Arg Ser Arg Val Thr Gln Asp Ala Asn Ala Thr
        265                 270                 275

ctc tgg gcc ttc ctg cag tgg cgc cgg ggg ctg tgg gcg cag cgg ccc       918
Leu Trp Ala Phe Leu Gln Trp Arg Arg Gly Leu Trp Ala Gln Arg Pro
    280                 285                 290

cac gac tcc gcg cag ctg ctc acg ggc cgc gcc ttc cag ggc gcc aca       966
His Asp Ser Ala Gln Leu Leu Thr Gly Arg Ala Phe Gln Gly Ala Thr
295                 300                 305                 310

gtg ggc ctg gcg ccc gtc gag ggc atg tgc cgc gcc gag agc tcg gga      1014
Val Gly Leu Ala Pro Val Glu Gly Met Cys Arg Ala Glu Ser Ser Gly
            315                 320                 325

ggc gtg agc acg gac cac tcg gag ctc ccc atc ggc gcc gca gcc acc      1062
Gly Val Ser Thr Asp His Ser Glu Leu Pro Ile Gly Ala Ala Ala Thr
            330                 335                 340

atg gcc cat gag atc ggc cac agc ctc ggc ctc agc cac gac ccc gac      1110
Met Ala His Glu Ile Gly His Ser Leu Gly Leu Ser His Asp Pro Asp
        345                 350                 355

ggc tgc tgc gtg gag gct gcg gcc gag tcc gga ggc tgc gtc atg gct      1158
Gly Cys Cys Val Glu Ala Ala Ala Glu Ser Gly Gly Cys Val Met Ala
    360                 365                 370

gcg gcc acc ggg cac ccg ttt ccg cgc gtg ttc agc gcc tgc agc cgc      1206
Ala Ala Thr Gly His Pro Phe Pro Arg Val Phe Ser Ala Cys Ser Arg
375                 380                 385                 390

cgc cag ctg cgc gcc ttc ttc cgc aag ggg ggc ggc gct tgc ctc tcc      1254
Arg Gln Leu Arg Ala Phe Phe Arg Lys Gly Gly Gly Ala Cys Leu Ser
                395                 400                 405

aat gcc ccg gac ccc gga ctc ccg gtg ccg ccg gcg ctc tgc ggg aac      1302
Asn Ala Pro Asp Pro Gly Leu Pro Val Pro Pro Ala Leu Cys Gly Asn
            410                 415                 420

ggc ttc gtg gaa gcg ggc gag gag tgt gac tgc ggc cct ggc cag gag      1350
Gly Phe Val Glu Ala Gly Glu Glu Cys Asp Cys Gly Pro Gly Gln Glu
        425                 430                 435

tgc cgc gac ctc tgc tgc ttt gct cac aac tgc tcg ctg cgc ccg ggg      1398
Cys Arg Asp Leu Cys Cys Phe Ala His Asn Cys Ser Leu Arg Pro Gly
    440                 445                 450

gcc cag tgc gcc cac ggg gac tgc tgc gtg cgc tgc ctg ctg aag ccg      1446
Ala Gln Cys Ala His Gly Asp Cys Cys Val Arg Cys Leu Leu Lys Pro
455                 460                 465                 470

gct gga gcg ctg tgc cgc cag gcc atg ggt gac tgt gac ctc cct gag      1494
Ala Gly Ala Leu Cys Arg Gln Ala Met Gly Asp Cys Asp Leu Pro Glu
                475                 480                 485

ttt tgc acg ggc acc tcc tcc cac tgt ccc cca gac gtt tac cta ctg      1542
Phe Cys Thr Gly Thr Ser Ser His Cys Pro Pro Asp Val Tyr Leu Leu
            490                 495                 500

gac ggc tca ccc tgt gcc agg ggc agt ggc tac tgc tgg gat ggc gca      1590
Asp Gly Ser Pro Cys Ala Arg Gly Ser Gly Tyr Cys Trp Asp Gly Ala
        505                 510                 515

tgt ccc acg ctg gag cag cag tgc cag cag ctc tgg ggg cct ggc tcc      1638
Cys Pro Thr Leu Glu Gln Gln Cys Gln Gln Leu Trp Gly Pro Gly Ser
    520                 525                 530

cac cca gct ccc gag gcc tgt ttc cag gtg gtg aac tct gcg gga gat      1686
His Pro Ala Pro Glu Ala Cys Phe Gln Val Val Asn Ser Ala Gly Asp
535                 540                 545                 550

gct cat gga aac tgc ggc cag gac agc gag ggc cac ttc ctg ccc tgt      1734
Ala His Gly Asn Cys Gly Gln Asp Ser Glu Gly His Phe Leu Pro Cys
                555                 560                 565
```

-continued

```
gca ggg agg gat gcc ctg tgt ggg aag ctg cag tgc cag ggt gga aag     1782
Ala Gly Arg Asp Ala Leu Cys Gly Lys Leu Gln Cys Gln Gly Gly Lys
            570                 575                 580

ccc agc ctg ctc gca ccg cac atg gtg cca gtg gac tct acc gtt cac     1830
Pro Ser Leu Leu Ala Pro His Met Val Pro Val Asp Ser Thr Val His
        585                 590                 595

cta gat ggc cag gaa gtg act tgt cgg gga gcc ttg gca ctc ccc agt     1878
Leu Asp Gly Gln Glu Val Thr Cys Arg Gly Ala Leu Ala Leu Pro Ser
    600                 605                 610

gcc cag ctg gac ctg ctt ggc ctg ggc ctg gta gag cca ggc acc cag     1926
Ala Gln Leu Asp Leu Leu Gly Leu Gly Leu Val Glu Pro Gly Thr Gln
615                 620                 625                 630

tgt gga cct aga atg gtg tgc cag agc agg cgc tgc agg aag aat gcc     1974
Cys Gly Pro Arg Met Val Cys Gln Ser Arg Arg Cys Arg Lys Asn Ala
                635                 640                 645

ttc cag gag ctt cag cgc tgc ctg act gcc tgc cac agc cac ggg gct     2022
Phe Gln Glu Leu Gln Arg Cys Leu Thr Ala Cys His Ser His Gly Ala
            650                 655                 660

ggg ctc cac cct tct gtg aca agc cag gct ttg gtg gca gca tgg aca     2070
Gly Leu His Pro Ser Val Thr Ser Gln Ala Leu Val Ala Ala Trp Thr
        665                 670                 675

gtg gcc ctg tgc agg ctg aaa acc atg aca cct tcc tgc tgg cca tgc     2118
Val Ala Leu Cys Arg Leu Lys Thr Met Thr Pro Ser Cys Trp Pro Cys
    680                 685                 690

tcc tca gcg tcc tgc tgc ctc tgc tcc cag ggg ccg gcc tgg cct ggt     2166
Ser Ser Ala Ser Cys Cys Leu Cys Ser Gln Gly Pro Ala Trp Pro Gly
695                 700                 705                 710

gtt gct acc gac tcc cag gag ccc atc tgc agc gat gca gct ggg gct     2214
Val Ala Thr Asp Ser Gln Glu Pro Ile Cys Ser Asp Ala Ala Gly Ala
                715                 720                 725

gca gaa ggg acc ctg cgt gca gtg gcc cca aag atg gcc cac aca ggg     2262
Ala Glu Gly Thr Leu Arg Ala Val Ala Pro Lys Met Ala His Thr Gly
            730                 735                 740

acc acc ccc tgg gcg gcg ttc acc cca tgg agt tgg gcc cca cag cca     2310
Thr Thr Pro Trp Ala Ala Phe Thr Pro Trp Ser Trp Ala Pro Gln Pro
        745                 750                 755

ctg gac agc cct ggc ccc tgg acc ctg aga act ctc atg agc cca gca     2358
Leu Asp Ser Pro Gly Pro Trp Thr Leu Arg Thr Leu Met Ser Pro Ala
    760                 765                 770

gcc acc ctg aga agc ctc tgc cag cag tct cgc ctg acc ccc aag atc     2406
Ala Thr Leu Arg Ser Leu Cys Gln Gln Ser Arg Leu Thr Pro Lys Ile
775                 780                 785                 790

aag tcc aga tgc caa gat cct gcc tct ggt gag agg tagctcctaa          2452
Lys Ser Arg Cys Gln Asp Pro Ala Ser Gly Glu Arg
                795                 800

aatgaacaga tttaaagaca ggtggccact gacagccact ccaggaactt gaactgcagg   2512

ggcagagcca gtgaatcacc ggacctccag cacctgcagg cagcttggaa gtttcttccc   2572

cgagtggagc ttcgacccac ccactccagg aacccagagc cacattagaa gttcctgagg   2632

gctggagaac actgctgggc acactctcca gctcaataaa ccatcagtcc cagaagcaaa   2692

ggtcacacag cccctgacct ccctcaccag tggaggctgg gtagtgctgg ccatcccaaa   2752

agggctctgt cctgggagtc tggtgtgtct cctacatgca atttccacgg acccagctct   2812

gtggagggca tgactgctgg ccagaagcta gtggtcctgg ggccctatgg ttcgactgag   2872

tccacactcc cctggagcct ggctggcctc tgcaaacaaa cataattttg gggaccttcc   2932

ttcctgtttc ttcccaccct gtcttctccc ctaggtggtt cctgagcccc cacccccaat   2992
```

-continued

```
cccagtgcta cacctgaggt tctggagctc agaatctgac agcctctccc ccattctgtg   3052

tgtgtcgggg ggacagaggg aaccatttaa gaaaagatac caaagtagaa gtcaaaagaa   3112

agacatgttg gctataggcg tggtggctca tgcctataat cccagcactt tgggaagccg   3172

gggtaggagg atcaccagag gccagcaggt ccacaccagc ctgggcaaca cagcaagaca   3232

ccgcatctac agaaaaattt taaaattagc tgggcgtggt ggtgtgtacc tgtaggccta   3292

gctgctcagg aggctgaagc aggaggatca cttgagcctg agttcaacac tgcagtgagc   3352

tatggtggca ccactgcact ccagcctggg tgacagagca agaccctgtc tctaaaataa   3412

attttaaaaa gacatatta                                                 3431
```

```
<210> SEQ ID NO 2
<211> LENGTH: 802
<212> TYPE: PRT
<213> ORGANISM: Homo sapiens

<400> SEQUENCE: 2

Met Gly Trp Arg Pro Arg Arg Ala Arg Gly Thr Pro Leu Leu Leu Leu
 1               5                  10                  15

Leu Leu Leu Leu Leu Leu Trp Pro Val Pro Gly Ala Gly Val Leu Gln
            20                  25                  30

Gly His Ile Pro Gly Gln Pro Val Thr Pro His Trp Val Leu Asp Gly
        35                  40                  45

Gln Pro Trp Arg Thr Val Ser Leu Glu Glu Pro Val Ser Lys Pro Asp
    50                  55                  60

Met Gly Leu Val Ala Leu Glu Ala Glu Gly Gln Glu Leu Leu Leu Glu
65                  70                  75                  80

Leu Glu Lys Asn His Arg Leu Leu Ala Pro Gly Tyr Ile Glu Thr His
                85                  90                  95

Tyr Gly Pro Asp Gly Gln Pro Val Val Leu Ala Pro Asn His Thr Asp
            100                 105                 110

His Cys His Tyr Gln Gly Arg Val Arg Gly Phe Pro Asp Ser Trp Val
        115                 120                 125

Val Leu Cys Thr Cys Ser Gly Met Ser Gly Leu Ile Thr Leu Ser Arg
    130                 135                 140

Asn Ala Ser Tyr Tyr Leu Arg Pro Trp Pro Pro Arg Gly Ser Lys Asp
145                 150                 155                 160

Phe Ser Thr His Glu Ile Phe Arg Met Glu Gln Leu Leu Thr Trp Lys
                165                 170                 175

Gly Thr Cys Gly His Arg Asp Pro Gly Asn Lys Ala Gly Met Thr Ser
            180                 185                 190

Leu Pro Gly Gly Pro Gln Ser Arg Gly Arg Arg Glu Ala Arg Arg Thr
        195                 200                 205

Arg Lys Tyr Leu Glu Leu Tyr Ile Val Ala Asp His Thr Leu Phe Leu
    210                 215                 220

Thr Arg His Arg Asn Leu Asn His Thr Lys Gln Arg Leu Leu Glu Val
225                 230                 235                 240

Ala Asn Tyr Val Asp Gln Leu Leu Arg Thr Leu Asp Ile Gln Val Ala
                245                 250                 255

Leu Thr Gly Leu Glu Val Trp Thr Glu Arg Asp Arg Ser Arg Val Thr
            260                 265                 270

Gln Asp Ala Asn Ala Thr Leu Trp Ala Phe Leu Gln Trp Arg Arg Gly
        275                 280                 285

Leu Trp Ala Gln Arg Pro His Asp Ser Ala Gln Leu Leu Thr Gly Arg
```

-continued

```
    290                 295                 300

Ala Phe Gln Gly Ala Thr Val Gly Leu Ala Pro Val Glu Gly Met Cys
305                 310                 315                 320

Arg Ala Glu Ser Ser Gly Gly Val Ser Thr Asp His Ser Glu Leu Pro
                325                 330                 335

Ile Gly Ala Ala Ala Thr Met Ala His Glu Ile Gly His Ser Leu Gly
            340                 345                 350

Leu Ser His Asp Pro Asp Gly Cys Cys Val Glu Ala Ala Ala Glu Ser
        355                 360                 365

Gly Gly Cys Val Met Ala Ala Ala Thr Gly His Pro Phe Pro Arg Val
    370                 375                 380

Phe Ser Ala Cys Ser Arg Arg Gln Leu Arg Ala Phe Phe Arg Lys Gly
385                 390                 395                 400

Gly Gly Ala Cys Leu Ser Asn Ala Pro Asp Pro Gly Leu Pro Val Pro
                405                 410                 415

Pro Ala Leu Cys Gly Asn Gly Phe Val Glu Ala Gly Glu Glu Cys Asp
            420                 425                 430

Cys Gly Pro Gly Gln Glu Cys Arg Asp Leu Cys Cys Phe Ala His Asn
        435                 440                 445

Cys Ser Leu Arg Pro Gly Ala Gln Cys Ala His Gly Asp Cys Cys Val
    450                 455                 460

Arg Cys Leu Leu Lys Pro Ala Gly Ala Leu Cys Arg Gln Ala Met Gly
465                 470                 475                 480

Asp Cys Asp Leu Pro Glu Phe Cys Thr Gly Thr Ser Ser His Cys Pro
                485                 490                 495

Pro Asp Val Tyr Leu Leu Asp Gly Ser Pro Cys Ala Arg Gly Ser Gly
            500                 505                 510

Tyr Cys Trp Asp Gly Ala Cys Pro Thr Leu Glu Gln Gln Cys Gln Gln
        515                 520                 525

Leu Trp Gly Pro Gly Ser His Pro Ala Pro Glu Ala Cys Phe Gln Val
    530                 535                 540

Val Asn Ser Ala Gly Asp Ala His Gly Asn Cys Gly Gln Asp Ser Glu
545                 550                 555                 560

Gly His Phe Leu Pro Cys Ala Gly Arg Asp Ala Leu Cys Gly Lys Leu
                565                 570                 575

Gln Cys Gln Gly Gly Lys Pro Ser Leu Leu Ala Pro His Met Val Pro
            580                 585                 590

Val Asp Ser Thr Val His Leu Asp Gly Gln Glu Val Thr Cys Arg Gly
        595                 600                 605

Ala Leu Ala Leu Pro Ser Ala Gln Leu Asp Leu Leu Gly Leu Gly Leu
    610                 615                 620

Val Glu Pro Gly Thr Gln Cys Gly Pro Arg Met Val Cys Gln Ser Arg
625                 630                 635                 640

Arg Cys Arg Lys Asn Ala Phe Gln Glu Leu Gln Arg Cys Leu Thr Ala
                645                 650                 655

Cys His Ser His Gly Ala Gly Leu His Pro Ser Val Thr Ser Gln Ala
            660                 665                 670

Leu Val Ala Ala Trp Thr Val Ala Leu Cys Arg Leu Lys Thr Met Thr
        675                 680                 685

Pro Ser Cys Trp Pro Cys Ser Ser Ala Ser Cys Cys Leu Cys Ser Gln
    690                 695                 700

Gly Pro Ala Trp Pro Gly Val Ala Thr Asp Ser Gln Glu Pro Ile Cys
705                 710                 715                 720
```

-continued

Ser Asp Ala Ala Gly Ala Ala Glu Gly Thr Leu Arg Ala Val Ala Pro
725 730 735

Lys Met Ala His Thr Gly Thr Thr Pro Trp Ala Ala Phe Thr Pro Trp
740 745 750

Ser Trp Ala Pro Gln Pro Leu Asp Ser Pro Gly Pro Trp Thr Leu Arg
755 760 765

Thr Leu Met Ser Pro Ala Ala Thr Leu Arg Ser Leu Cys Gln Gln Ser
770 775 780

Arg Leu Thr Pro Lys Ile Lys Ser Arg Cys Gln Asp Pro Ala Ser Gly
785 790 795 800

Glu Arg

<210> SEQ ID NO 3
<211> LENGTH: 3468
<212> TYPE: DNA
<213> ORGANISM: Homo sapiens
<220> FEATURE:
<221> NAME/KEY: CDS
<222> LOCATION: (37)...(2472)

<400> SEQUENCE: 3
gcgagccgct gcctagaggc cgaggagctc acagct atg ggc tgg agg ccc cgg 54
Met Gly Trp Arg Pro Arg
1 5 aga gct cgg ggg acc ccg ttg ctg ctg ctg cta cta ctg ctg ctg ctc 102
Arg Ala Arg Gly Thr Pro Leu Leu Leu Leu Leu Leu Leu Leu Leu Leu
10 15 20 tgg cca gtg cca ggc gcc ggg gtg ctt caa gga cat atc cct ggg cag 150
Trp Pro Val Pro Gly Ala Gly Val Leu Gln Gly His Ile Pro Gly Gln
25 30 35 cca gtc acc ccg cac tgg gtc ctg gat gga caa ccc tgg cgc acc gtc 198
Pro Val Thr Pro His Trp Val Leu Asp Gly Gln Pro Trp Arg Thr Val
40 45 50 agc ctg gag gag ccg gtc tcg aag cca gac atg ggg ctg gtg gcc ctg 246
Ser Leu Glu Glu Pro Val Ser Lys Pro Asp Met Gly Leu Val Ala Leu
55 60 65 70 gag gct gaa ggc cag gag ctc ctg ctt gag ctg gag aag aac cac agg 294
Glu Ala Glu Gly Gln Glu Leu Leu Leu Glu Leu Glu Lys Asn His Arg
75 80 85 ctg ctg gcc cca gga tac ata gaa acc cac tac ggc cca gat ggg cag 342
Leu Leu Ala Pro Gly Tyr Ile Glu Thr His Tyr Gly Pro Asp Gly Gln
90 95 100 cca gtg gtg ctg gcc ccc aac cac acg gat cat tgc cac tac caa ggg 390
Pro Val Val Leu Ala Pro Asn His Thr Asp His Cys His Tyr Gln Gly
105 110 115 cga gta agg ggc ttc ccc gac tcc tgg gta gtc ctc tgc acc tgc tct 438
Arg Val Arg Gly Phe Pro Asp Ser Trp Val Val Leu Cys Thr Cys Ser
120 125 130 ggg atg agt ggc ctg atc acc ctc agc agg aat gcc agc tat tat ctg 486
Gly Met Ser Gly Leu Ile Thr Leu Ser Arg Asn Ala Ser Tyr Tyr Leu
135 140 145 150 cgt ccc tgg cca ccc cgg ggc tcc aag gac ttc tca acc cac gag atc 534
Arg Pro Trp Pro Pro Arg Gly Ser Lys Asp Phe Ser Thr His Glu Ile
155 160 165 ttt cgg atg gag cag ctg ctc acc tgg aaa gga acc tgt ggc cac agg 582
Phe Arg Met Glu Gln Leu Leu Thr Trp Lys Gly Thr Cys Gly His Arg
170 175 180 gat cct ggg aac aaa gcg ggc atg acc agc ctt cct ggt ggt ccc cag 630
Asp Pro Gly Asn Lys Ala Gly Met Thr Ser Leu Pro Gly Gly Pro Gln -continued

```
        185                 190                 195

agc agg ggc agg cga gaa gcg cgc agg acc cgg aag tac ctg gaa ctg       678
Ser Arg Gly Arg Arg Glu Ala Arg Arg Thr Arg Lys Tyr Leu Glu Leu
    200                 205                 210

tac att gtg gca gac cac acc ctg ttc ttg act cgg cac cga aac ttg       726
Tyr Ile Val Ala Asp His Thr Leu Phe Leu Thr Arg His Arg Asn Leu
215                 220                 225                 230

aac cac acc aaa cag cgt ctc ctg gaa gtc gcc aac tac gtg gac cag       774
Asn His Thr Lys Gln Arg Leu Leu Glu Val Ala Asn Tyr Val Asp Gln
                235                 240                 245

ctt ctc agg act ctg gac att cag gtg gcg ctg acc ggc ctg gag gtg       822
Leu Leu Arg Thr Leu Asp Ile Gln Val Ala Leu Thr Gly Leu Glu Val
            250                 255                 260

tgg acc gag cgg gac cgc agc cgc gtc acg cag gac gcc aac gcc acg       870
Trp Thr Glu Arg Asp Arg Ser Arg Val Thr Gln Asp Ala Asn Ala Thr
        265                 270                 275

ctc tgg gcc ttc ctg cag tgg cgc cgg ggg ctg tgg gcg cag cgg ccc       918
Leu Trp Ala Phe Leu Gln Trp Arg Arg Gly Leu Trp Ala Gln Arg Pro
    280                 285                 290

cac gac tcc gcg cag ctg ctc acg ggc cgc gcc ttc cag ggc gcc aca       966
His Asp Ser Ala Gln Leu Leu Thr Gly Arg Ala Phe Gln Gly Ala Thr
295                 300                 305                 310

gtg ggc ctg gcg ccc gtc gag ggc atg tgc cgc gcc gag agc tcg gga      1014
Val Gly Leu Ala Pro Val Glu Gly Met Cys Arg Ala Glu Ser Ser Gly
                315                 320                 325

ggc gtg agc acg gac cac tcg gag ctc ccc atc ggc gcc gca gcc acc      1062
Gly Val Ser Thr Asp His Ser Glu Leu Pro Ile Gly Ala Ala Ala Thr
            330                 335                 340

atg gcc cat gag atc ggc cac agc ctc ggc ctc agc cac gac ccc gac      1110
Met Ala His Glu Ile Gly His Ser Leu Gly Leu Ser His Asp Pro Asp
        345                 350                 355

ggc tgc tgc gtg gag gct gcg gcc gag tcc gga ggc tgc gtc atg gct      1158
Gly Cys Cys Val Glu Ala Ala Ala Glu Ser Gly Gly Cys Val Met Ala
    360                 365                 370

gcg gcc acc ggg cac ccg ttt ccg cgc gtg ttc agc gcc tgc agc cgc      1206
Ala Ala Thr Gly His Pro Phe Pro Arg Val Phe Ser Ala Cys Ser Arg
375                 380                 385                 390

cgc cag ctg cgc gcc ttc ttc cgc aag ggg ggc ggc gct tgc ctc tcc      1254
Arg Gln Leu Arg Ala Phe Phe Arg Lys Gly Gly Gly Ala Cys Leu Ser
                395                 400                 405

aat gcc ccg gac ccc gga ctc ccg gtg ccg ccg gcg ctc tgc ggg aac      1302
Asn Ala Pro Asp Pro Gly Leu Pro Val Pro Pro Ala Leu Cys Gly Asn
            410                 415                 420

ggc ttc gtg gaa gcg ggc gag gag tgt gac tgc ggc cct ggc cag gag      1350
Gly Phe Val Glu Ala Gly Glu Glu Cys Asp Cys Gly Pro Gly Gln Glu
        425                 430                 435

tgc cgc gac ctc tgc tgc ttt gct cac aac tgc tcg ctg cgc ccg ggg      1398
Cys Arg Asp Leu Cys Cys Phe Ala His Asn Cys Ser Leu Arg Pro Gly
    440                 445                 450

gcc cag tgc gcc cac ggg gac tgc tgc gtg cgc tgc ctg ctg aag ccg      1446
Ala Gln Cys Ala His Gly Asp Cys Cys Val Arg Cys Leu Leu Lys Pro
455                 460                 465                 470

gct gga gcg ctg tgc cgc cag gcc atg ggt gac tgt gac ctc cct gag      1494
Ala Gly Ala Leu Cys Arg Gln Ala Met Gly Asp Cys Asp Leu Pro Glu
                475                 480                 485

ttt tgc acg ggc acc tcc tcc cac tgt ccc cca gac gtt tac cta ctg      1542
Phe Cys Thr Gly Thr Ser Ser His Cys Pro Pro Asp Val Tyr Leu Leu
            490                 495                 500

gac ggc tca ccc tgt gcc agg ggc agt ggc tac tgc tgg gat ggc gca      1590
```

-continued

```
Asp Gly Ser Pro Cys Ala Arg Gly Ser Gly Tyr Cys Trp Asp Gly Ala
        505                 510                 515

tgt ccc acg ctg gag cag cag tgc cag cag ctc tgg ggg cct ggc tcc      1638
Cys Pro Thr Leu Glu Gln Gln Cys Gln Gln Leu Trp Gly Pro Gly Ser
    520                 525                 530

cac cca gct ccc gag gcc tgt ttc cag gtg gtg aac tct gcg gga gat      1686
His Pro Ala Pro Glu Ala Cys Phe Gln Val Val Asn Ser Ala Gly Asp
535                 540                 545                 550

gct cat gga aac tgc ggc cag gac agc gag ggc cac ttc ctg ccc tgt      1734
Ala His Gly Asn Cys Gly Gln Asp Ser Glu Gly His Phe Leu Pro Cys
                555                 560                 565

gca ggg agg gat gcc ctg tgt ggg aag ctg cag tgc cag ggt gga aag      1782
Ala Gly Arg Asp Ala Leu Cys Gly Lys Leu Gln Cys Gln Gly Gly Lys
            570                 575                 580

ccc agc ctg ctc gca ccg cac atg gtg cca gtg gac tct acc gtt cac      1830
Pro Ser Leu Leu Ala Pro His Met Val Pro Val Asp Ser Thr Val His
        585                 590                 595

cta gat ggc cag gaa gtg act tgt cgg gga gcc ttg gca ctc ccc agt      1878
Leu Asp Gly Gln Glu Val Thr Cys Arg Gly Ala Leu Ala Leu Pro Ser
    600                 605                 610

gcc cag ctg gac ctg ctt ggc ctg ggc ctg gta gag cca ggc acc cag      1926
Ala Gln Leu Asp Leu Leu Gly Leu Gly Leu Val Glu Pro Gly Thr Gln
615                 620                 625                 630

tgt gga cct aga atg gtg tgc cag agc agg cgc tgc agg aag aat gcc      1974
Cys Gly Pro Arg Met Val Cys Gln Ser Arg Arg Cys Arg Lys Asn Ala
                635                 640                 645

ttc cag gag ctt cag cgc tgc ctg act gcc tgc cac agc cac ggg gtt      2022
Phe Gln Glu Leu Gln Arg Cys Leu Thr Ala Cys His Ser His Gly Val
            650                 655                 660

tgc aat agc aac cat aac tgc cac tgt gct cca ggc tgg gct cca ccc      2070
Cys Asn Ser Asn His Asn Cys His Cys Ala Pro Gly Trp Ala Pro Pro
        665                 670                 675

ttc tgt gac aag cca ggc ttt ggt ggc agc atg gac agt ggc cct gtg      2118
Phe Cys Asp Lys Pro Gly Phe Gly Gly Ser Met Asp Ser Gly Pro Val
    680                 685                 690

cag gct gaa aac cat gac acc ttc ctg ctg gcc atg ctc ctc agc gtc      2166
Gln Ala Glu Asn His Asp Thr Phe Leu Leu Ala Met Leu Leu Ser Val
695                 700                 705                 710

ctg ctg cct ctg ctc cca ggg gcc ggc ctg gcc tgg tgt tgc tac cga      2214
Leu Leu Pro Leu Leu Pro Gly Ala Gly Leu Ala Trp Cys Cys Tyr Arg
                715                 720                 725

ctc cca gga gcc cat ctg cag cga tgc agc tgg ggc tgc aga agg gac      2262
Leu Pro Gly Ala His Leu Gln Arg Cys Ser Trp Gly Cys Arg Arg Asp
            730                 735                 740

cct gcg tgc agt ggc ccc aaa gat ggc cca cac agg gac cac ccc ctg      2310
Pro Ala Cys Ser Gly Pro Lys Asp Gly Pro His Arg Asp His Pro Leu
        745                 750                 755

ggc ggc gtt cac ccc atg gag ttg ggc ccc aca gcc act gga cag ccc      2358
Gly Gly Val His Pro Met Glu Leu Gly Pro Thr Ala Thr Gly Gln Pro
    760                 765                 770

tgg ccc ctg gac cct gag aac tct cat gag ccc agc agc cac cct gag      2406
Trp Pro Leu Asp Pro Glu Asn Ser His Glu Pro Ser Ser His Pro Glu
775                 780                 785                 790

aag cct ctg cca gca gtc tcg cct gac ccc caa gat caa gtc cag atg      2454
Lys Pro Leu Pro Ala Val Ser Pro Asp Pro Gln Asp Gln Val Gln Met
                795                 800                 805

cca aga tcc tgc ctc tgg tgagaggtag ctcctaaaat gaacagattt             2502
Pro Arg Ser Cys Leu Trp
            810
```

-continued

```
aaagacaggt ggccactgac agccactcca ggaacttgaa ctgcaggggc agagccagtg   2562

aatcaccgga cctccagcac ctgcaggcag cttggaagtt tcttccccga gtggagcttc   2622

gacccaccca ctccaggaac ccagagccac attagaagtt cctgagggct ggagaacact   2682

gctgggcaca ctctccagct caataaacca tcagtcccag aagcaaaggt cacacagccc   2742

ctgacctccc tcaccagtgg aggctgggta gtgctggcca tcccaaaagg gctctgtcct   2802

gggagtctgg tgtgtctcct acatgcaatt tccacggacc cagctctgtg gagggcatga   2862

ctgctggcca gaagctagtg gtcctggggc cctatggttc gactgagtcc acactcccct   2922

ggagcctggc tggcctctgc aaacaaacat aattttgggg accttccttc ctgtttcttc   2982

ccaccctgtc ttctccccta ggtggttcct gagcccccac ccccaatccc agtgctacac   3042

ctgaggttct ggagctcaga atctgacagc ctctccccca ttctgtgtgt gtcgggggga   3102

cagagggaac catttaagaa aagataccaa agtagaagtc aaaagaaaga catgttggct   3162

ataggcgtgg tggctcatgc ctataatccc agcactttgg gaagccgggg taggaggatc   3222

accagaggcc agcaggtcca caccagcctg ggcaacacag caagacaccg catctacaga   3282

aaaattttaa aattagctgg gcgtggtggt gtgtacctgt aggcctagct gctcaggagg   3342

ctgaagcagg aggatcactt gagcctgagt tcaacactgc agtgagctat ggtggcacca   3402

ctgcactcca gcctgggtga cagagcaaga ccctgtctct aaaataaatt ttaaaaagac   3462

atatta                                                              3468
```

```
<210> SEQ ID NO 4
<211> LENGTH: 812
<212> TYPE: PRT
<213> ORGANISM: Homo sapiens

<400> SEQUENCE: 4

Met Gly Trp Arg Pro Arg Arg Ala Arg Gly Thr Pro Leu Leu Leu Leu
 1               5                  10                  15

Leu Leu Leu Leu Leu Leu Trp Pro Val Pro Gly Ala Gly Val Leu Gln
            20                  25                  30

Gly His Ile Pro Gly Gln Pro Val Thr Pro His Trp Val Leu Asp Gly
        35                  40                  45

Gln Pro Trp Arg Thr Val Ser Leu Glu Glu Pro Val Ser Lys Pro Asp
    50                  55                  60

Met Gly Leu Val Ala Leu Glu Ala Glu Gly Gln Glu Leu Leu Leu Glu
65                  70                  75                  80

Leu Glu Lys Asn His Arg Leu Leu Ala Pro Gly Tyr Ile Glu Thr His
                85                  90                  95

Tyr Gly Pro Asp Gly Gln Pro Val Val Leu Ala Pro Asn His Thr Asp
            100                 105                 110

His Cys His Tyr Gln Gly Arg Val Arg Gly Phe Pro Asp Ser Trp Val
        115                 120                 125

Val Leu Cys Thr Cys Ser Gly Met Ser Gly Leu Ile Thr Leu Ser Arg
    130                 135                 140

Asn Ala Ser Tyr Tyr Leu Arg Pro Trp Pro Pro Arg Gly Ser Lys Asp
145                 150                 155                 160

Phe Ser Thr His Glu Ile Phe Arg Met Glu Gln Leu Leu Thr Trp Lys
                165                 170                 175

Gly Thr Cys Gly His Arg Asp Pro Gly Asn Lys Ala Gly Met Thr Ser
            180                 185                 190

Leu Pro Gly Gly Pro Gln Ser Arg Gly Arg Arg Glu Ala Arg Arg Thr
```

-continued

```
        195                 200                 205

Arg Lys Tyr Leu Glu Leu Tyr Ile Val Ala Asp His Thr Leu Phe Leu
    210                 215                 220

Thr Arg His Arg Asn Leu Asn His Thr Lys Gln Arg Leu Leu Glu Val
225                 230                 235                 240

Ala Asn Tyr Val Asp Gln Leu Leu Arg Thr Leu Asp Ile Gln Val Ala
                245                 250                 255

Leu Thr Gly Leu Glu Val Trp Thr Glu Arg Asp Arg Ser Arg Val Thr
            260                 265                 270

Gln Asp Ala Asn Ala Thr Leu Trp Ala Phe Leu Gln Trp Arg Arg Gly
        275                 280                 285

Leu Trp Ala Gln Arg Pro His Asp Ser Ala Gln Leu Leu Thr Gly Arg
    290                 295                 300

Ala Phe Gln Gly Ala Thr Val Gly Leu Ala Pro Val Glu Gly Met Cys
305                 310                 315                 320

Arg Ala Glu Ser Ser Gly Gly Val Ser Thr Asp His Ser Glu Leu Pro
                325                 330                 335

Ile Gly Ala Ala Ala Thr Met Ala His Glu Ile Gly His Ser Leu Gly
            340                 345                 350

Leu Ser His Asp Pro Asp Gly Cys Cys Val Glu Ala Ala Ala Glu Ser
        355                 360                 365

Gly Gly Cys Val Met Ala Ala Ala Thr Gly His Pro Phe Pro Arg Val
    370                 375                 380

Phe Ser Ala Cys Ser Arg Arg Gln Leu Arg Ala Phe Phe Arg Lys Gly
385                 390                 395                 400

Gly Gly Ala Cys Leu Ser Asn Ala Pro Asp Pro Gly Leu Pro Val Pro
                405                 410                 415

Pro Ala Leu Cys Gly Asn Gly Phe Val Glu Ala Gly Glu Glu Cys Asp
            420                 425                 430

Cys Gly Pro Gly Gln Glu Cys Arg Asp Leu Cys Cys Phe Ala His Asn
        435                 440                 445

Cys Ser Leu Arg Pro Gly Ala Gln Cys Ala His Gly Asp Cys Cys Val
    450                 455                 460

Arg Cys Leu Leu Lys Pro Ala Gly Ala Leu Cys Arg Gln Ala Met Gly
465                 470                 475                 480

Asp Cys Asp Leu Pro Glu Phe Cys Thr Gly Thr Ser Ser His Cys Pro
                485                 490                 495

Pro Asp Val Tyr Leu Leu Asp Gly Ser Pro Cys Ala Arg Gly Ser Gly
            500                 505                 510

Tyr Cys Trp Asp Gly Ala Cys Pro Thr Leu Glu Gln Gln Cys Gln Gln
        515                 520                 525

Leu Trp Gly Pro Gly Ser His Pro Ala Pro Glu Ala Cys Phe Gln Val
    530                 535                 540

Val Asn Ser Ala Gly Asp Ala His Gly Asn Cys Gly Gln Asp Ser Glu
545                 550                 555                 560

Gly His Phe Leu Pro Cys Ala Gly Arg Asp Ala Leu Cys Gly Lys Leu
                565                 570                 575

Gln Cys Gln Gly Gly Lys Pro Ser Leu Leu Ala Pro His Met Val Pro
            580                 585                 590

Val Asp Ser Thr Val His Leu Asp Gly Gln Glu Val Thr Cys Arg Gly
        595                 600                 605

Ala Leu Ala Leu Pro Ser Ala Gln Leu Asp Leu Leu Gly Leu Gly Leu
    610                 615                 620
```

-continued

```
Val Glu Pro Gly Thr Gln Cys Gly Pro Arg Met Val Cys Gln Ser Arg
625                 630                 635                 640

Arg Cys Arg Lys Asn Ala Phe Gln Glu Leu Gln Arg Cys Leu Thr Ala
                645                 650                 655

Cys His Ser His Gly Val Cys Asn Ser Asn His Asn Cys His Cys Ala
            660                 665                 670

Pro Gly Trp Ala Pro Pro Phe Cys Asp Lys Pro Gly Phe Gly Gly Ser
        675                 680                 685

Met Asp Ser Gly Pro Val Gln Ala Glu Asn His Asp Thr Phe Leu Leu
    690                 695                 700

Ala Met Leu Leu Ser Val Leu Leu Pro Leu Leu Pro Gly Ala Gly Leu
705                 710                 715                 720

Ala Trp Cys Cys Tyr Arg Leu Pro Gly Ala His Leu Gln Arg Cys Ser
                725                 730                 735

Trp Gly Cys Arg Arg Asp Pro Ala Cys Ser Gly Pro Lys Asp Gly Pro
            740                 745                 750

His Arg Asp His Pro Leu Gly Gly Val His Pro Met Glu Leu Gly Pro
        755                 760                 765

Thr Ala Thr Gly Gln Pro Trp Pro Leu Asp Pro Glu Asn Ser His Glu
    770                 775                 780

Pro Ser Ser His Pro Glu Lys Pro Leu Pro Ala Val Ser Pro Asp Pro
785                 790                 795                 800

Gln Asp Gln Val Gln Met Pro Arg Ser Cys Leu Trp
                805                 810
```

```
<210> SEQ ID NO 5
<211> LENGTH: 2406
<212> TYPE: DNA
<213> ORGANISM: Artificial Sequence
<220> FEATURE:
<223> OTHER INFORMATION: Degenerate sequence
<221> NAME/KEY: misc_feature
<222> LOCATION: (1)...(2406)
<223> OTHER INFORMATION: n = A,T,C or G

<400> SEQUENCE: 5

atgggntggm gnccnmgnmg ngcnmgnggn acnccnytny tnytnytnyt nytnytnytn      60

ytnytntggc cngtnccngg ngcnggngtn ytncarggnc ayathccngg ncarccngtn     120

acnccncayt gggtnytnga yggncarccn tggmgnacng tnwsnytnga rgarccngtn     180

wsnaarccng ayatgggnyt ngtngcnytn gargcngarg gncargaryt nytnytngar     240

ytngaraara aycaymgnyt nytngcnccn ggntayathg aracncayta yggnccngay     300

ggncarccng tngtnytngc nccnaaycay acngaycayt gycaytayca rggnmgngtn     360

mgnggnttyc cngaywsntg ggtngtnytn tgyacntgyw snggnatgws nggnytnath     420

acnytnwsnm gnaaygcnws ntaytayytn mgnccntggc cnccnmgngg nwsnaargay     480

ttywsnacnc aygarathtt ymgnatggar carytnytna cntggaargg nacntgyggn     540

caymgngayc cnggnaayaa rgcnggnatg acnwsnytnc cnggnggncc ncarwsnmgn     600

ggnmgnmgng argcnmgnmg nacnmgnaar tayytngary tntayathgt ngcngaycay     660

acnytnttyy tnacnmgnca ymgnaayytn aaycayacna arcarmgnyt nytngargtn     720

gcnaaytayg tngaycaryt nytnmgnacn ytngayathc argtngcnyt nacnggnytn     780

gargtntgga cngarmgnga ymgnwsnmgn gtnacncarg aygcnaaygc nacnytntgg     840

gcnttyytnc artggmgnmg nggnytntgg gcncarmgnc cncaygayws ngcncarytn     900
```

-continued

```
ytnacnggnm gngcnttyca rggngcnacn gtnggnytng cnccngtnga rggnatgtgy    960
mgngcngarw snwsnggngg ngtnwsnacn gaycaywsng arytnccnat hggngcngcn   1020
gcnacnatgg cncaygarat hggncaywsn ytnggnytnw sncaygaycc ngayggntgy   1080
tgygtngarg cngcngcnga rwsnggnggn tgygtnatgg cngcngcnac nggncayccn   1140
ttyccnmgng tnttywsngc ntgywsnmgn mgncarytnm gngcnttytt ymgnaarggn   1200
ggnggngcnt gyytnwsnaa ygcnccngay ccnggnytnc cngtnccncc ngcnytntgy   1260
ggnaayggnt tygtngargc nggngargar tgygaytgyg gnccnggnca rgartgymgn   1320
gayytntgyt gyttygcnca yaaytgywsn ytnmgnccng gngcncartg ygcncayggn   1380
gaytgytgyg tnmgntgyyt nytnaarccn gcnggngcny tntgymgnca rgcnatgggn   1440
gaytgygayy tnccngartt ytgyacnggn acnwsnwsnc aytgyccncc ngaygtntay   1500
ytnytngayg gnwsnccntg ygcnmgnggn wsnggntayt gytgggaygg ngcntgyccn   1560
acnytngarc arcartgyca rcarytntgg ggnccnggnw sncayccngc nccngargcn   1620
tgyttycarg tngtnaayws ngcnggngay gcncayggna aytgyggnca rgaywsngar   1680
ggncayttyy tnccntgygc nggnmgngay gcnytntgyg gnaarytnca rtgycarggn   1740
ggnaarccnw snytnytngc nccncayatg gtnccngtng aywsnacngt ncayytngay   1800
ggncargarg tnacntgymg nggngcnytn gcnytnccnw sngcncaryt ngayytnytn   1860
ggnytnggny tngtngarcc nggnacncar tgyggnccnm gnatggtntg ycarwsnmgn   1920
mgntgymgna araaygcntt ycargarytn carmgntgyy tnacngcntg ycaywsncay   1980
ggngcnggny tncayccnws ngtnacnwsn cargcnytng tngcngcntg gacngtngcn   2040
ytntgymgny tnaaracnat gacnccnwsn tgytggccnt gywsnwsngc nwsntgytgy   2100
ytntgywsnc arggnccngc ntggccnggn gtngcnacng aywsncarga rccnathtgy   2160
wsngaygcng cnggngcngc ngarggnacn ytnmgngcng tngcnccnaa ratggcncay   2220
acnggnacna cnccntgggc ngcnttyacn ccntggwsnt gggcnccnca rccnytngay   2280
wsnccnggnc cntggacnyt nmgnacnytn atgwsnccng cngcnacnyt nmgnwsnytn   2340
tgycarcarw snmgnytnac nccnaarath aarwsnmgnt gycargaycc ngcnwsnggn   2400
garmgn                                                              2406
```

<210> SEQ ID NO 6
<211> LENGTH: 2439
<212> TYPE: DNA
<213> ORGANISM: Artificial Sequence
<220> FEATURE:
<223> OTHER INFORMATION: Degenerate sequence
<221> NAME/KEY: misc_feature
<222> LOCATION: (1)...(2439)
<223> OTHER INFORMATION: n = A,T,C or G

<400> SEQUENCE: 6

```
atgggntggm gnccnmgnmg ngcnmgnggn acnccnytny tnytnytnyt nytnytnytn     60
ytnytntggc cngtnccngg ngcnggngtn ytncarggnc ayathccngg ncarccngtn    120
acnccncayt gggtnytnga yggncarccn tggmgnacng tnwsnytnga rgarccngtn    180
wsnaarccng ayatgggnyt ngtngcnytn gargcngarg gncargaryt nytnytngar    240
ytngaraara aycaymgnyt nytngcnccn ggntayathg aracncayta yggnccngay    300
ggncarccng tngtnytngc nccnaaycay acngaycayt gycaytayca rggnmgngtn    360
mgnggnttyc cngaywsntg ggtngtnytn tgyacntgyw snggnatgws nggnytnath    420
```

-continued

```
acnytnwsnm gnaaygcnws ntaytayytn mgnccntggc cnccnmgngg nwsnaargay    480
ttywsnacnc aygarathtt ymgnatggar carytnytna cntggaargg nacntgyggn    540
caymgngayc cnggnaayaa rgcnggnatg acnwsnytnc cnggnggncc ncarwsnmgn    600
ggnmgnmgng argcnmgnmg nacnmgnaar tayytngary tntayathgt ngcngaycay    660
acnytnttyy tnacnmgnca ymgnaayytn aaycayacna arcarmgnyt nytngargtn    720
gcnaaytayg tngaycaryt nytnmgnacn ytngayathc argtngcnyt nacnggnytn    780
gargtntgga cngarmgnga ymgnwsnmgn gtnacncarg aygcnaaygc nacnytntgg    840
gcnttyytnc artggmgnmg nggnytntgg gcncarmgnc cncaygayws ngcncarytn    900
ytnacnggnm gngcnttyca rggngcnacn gtnggnytng cnccngtnga rggnatgtgy    960
mgngcngarw snwsnggngg ngtnwsnacn gaycaywsng arytnccnat hggngcngcn   1020
gcnacnatgg cncaygarat hggncaywsn ytnggnytnw sncaygaycc ngayggntgy   1080
tgygtngarg cngcngcnga rwsnggnggn tgygtnatgg cngcngcnac nggncayccn   1140
ttyccnmgng tnttywsngc ntgywsnmgn mgncarytnm gngcnttytt ymgnaarggn   1200
ggnggngcnt gyytnwsnaa ygcnccngay ccnggnytnc cngtnccncc ngcnytntgy   1260
ggnaayggnt tygtngargc nggngargar tgygaytgyg gnccnggnca rgartgymgn   1320
gayytntgyt gyttygcnca yaaytgywsn ytnmgnccng gngcncartg ygcncayggn   1380
gaytgytgyg tnmgntgyyt nytnaarccn gcnggngcny tntgymgnca rgcnatgggn   1440
gaytgygayy tnccngartt ytgyacnggn acnwsnwsnc aytgyccncc ngaygtntay   1500
ytnytngayg gnwsnccntg ygcnmgnggn wsnggntayt gytgggaygg ngcntgyccn   1560
acnytngarc arcartgyca rcarytntgg ggnccnggnw sncayccngc nccngargcn   1620
tgyttycarg tngtnaayws ngcnggngay gcncayggna aytgyggnca rgaywsngar   1680
ggncayttyy tnccntgygc nggnmgngay gcnytntgyg gnaarytnca rtgycarggn   1740
ggnaarccnw snytnytngc nccncayatg gtnccngtng aywsnacngt ncayytngay   1800
ggncargarg tnacntgymg nggngcnytn gcnytnccnw sngcncaryt ngayytnytn   1860
ggnytnggny tngtngarcc nggnacncar tgyggnccnm gnatggtntg ycarwsnmgn   1920
mgntgymgna araaygcntt ycargarytn carmgntgyy tnacngcntg ycaywsncay   1980
ggngtntgya aywsnaayca yaaytgycay tgygcnccng gntgggcncc nccnttytgy   2040
gayaarccng gnttyggngg nwsnatggay wsnggnccng tncargcnga raaycaygay   2100
acnttyytny tngcnatgyt nytnwsngtn ytnytnccny tnytnccngg ngcnggnytn   2160
gcntggtgyt gytaymgnyt nccnggngcn cayytncarm gntgywsntg gggntgymgn   2220
mgngayccng cntgywsngg nccnaargay ggnccncaym gngaycaycc nytnggnggn   2280
gtncayccna tggarytngg nccnacngcn acnggncarc cntggccnyt ngayccngar   2340
aaywsncayg arccnwsnws ncayccngar aarccnytnc cngcngtnws nccngayccn   2400
cargaycarg tncaratgcc nmgnwsntgy ytntggtrr                          2439
```

<210> SEQ ID NO 7
<211> LENGTH: 23
<212> TYPE: DNA
<213> ORGANISM: Artificial Sequence
<220> FEATURE:
<223> OTHER INFORMATION: oligonucleotide ZC17,993

<400> SEQUENCE: 7

```
gaagctcctg gaaggcattc ttc                                             23
```

-continued

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide ZC17,994

<400> SEQUENCE: 8
tgacttgtcg gggagccttg g 21

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide API

<400> SEQUENCE: 9
ccatcctaat acgactcact atagggc 27

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide APII

<400> SEQUENCE: 10
actcactata gggctcgagc ggc 23

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide ZC18,262

<400> SEQUENCE: 11
gcaggaaggt gtcatggttt tcag 24

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide ZC22,481

<400> SEQUENCE: 12
aggccatggg tgactgtg 18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide ZC22,482

<400> SEQUENCE: 13
cgccatccca gcagtagc 18

<210> SEQ ID NO 14
<211> LENGTH: 4
<212> TYPE: PRT
<213> ORGANISM: Homo sapiens

-continued

<400> SEQUENCE: 14

Met Ser Glu Cys
 1

<210> SEQ ID NO 15
<211> LENGTH: 4
<212> TYPE: PRT
<213> ORGANISM: Homo sapiens

<400> SEQUENCE: 15

Arg Ser Glu Cys
 1

<210> SEQ ID NO 16
<211> LENGTH: 4
<212> TYPE: PRT
<213> ORGANISM: Homo sapiens

<400> SEQUENCE: 16

Ile Asp Asp Cys
 1

<210> SEQ ID NO 17
<211> LENGTH: 4
<212> TYPE: PRT
<213> ORGANISM: Homo sapiens

<400> SEQUENCE: 17

Arg Asp Asp Cys
 1

<210> SEQ ID NO 18
<211> LENGTH: 21
<212> TYPE: DNA
<213> ORGANISM: Artificial Sequence
<220> FEATURE:
<223> OTHER INFORMATION: oligonucleotide ZC18,604

<400> SEQUENCE: 18
cctgggagtc ggtagcaaca c 21

<210> SEQ ID NO 19
<211> LENGTH: 21
<212> TYPE: DNA
<213> ORGANISM: Artificial Sequence
<220> FEATURE:
<223> OTHER INFORMATION: oligonucleotide ZC18,605

<400> SEQUENCE: 19
gggctccacc cttctgtgac a 21

<210> SEQ ID NO 20
<211> LENGTH: 22
<212> TYPE: DNA
<213> ORGANISM: Artificial Sequence
<220> FEATURE:
<223> OTHER INFORMATION: ologonucleotide ZC20,646

<400> SEQUENCE: 20
gggagctggg attggtggtc ag 22

<210> SEQ ID NO 21
<211> LENGTH: 21
<212> TYPE: DNA
<213> ORGANISM: oligonucleotideArtificial Sequence -continued

```
<220> FEATURE:
<223> OTHER INFORMATION: oligonucleotide ZC20,634

<400> SEQUENCE: 21

agagcgtggc gttggcgtcc t                                             21


<210> SEQ ID NO 22
<211> LENGTH: 23
<212> TYPE: DNA
<213> ORGANISM: Artificial Sequence
<220> FEATURE:
<223> OTHER INFORMATION: oligonucleotide ZC20,633

<400> SEQUENCE: 22

ctgagaagct ggtccacgta gtt                                           23


<210> SEQ ID NO 23
<211> LENGTH: 20
<212> TYPE: DNA
<213> ORGANISM: Artificial Sequence
<220> FEATURE:
<223> OTHER INFORMATION: oligonucleotide ZC13,006

<400> SEQUENCE: 23

ggctgtcctc taagcgtcac                                               20


<210> SEQ ID NO 24
<211> LENGTH: 23
<212> TYPE: DNA
<213> ORGANISM: Artificial Sequence
<220> FEATURE:
<223> OTHER INFORMATION: ologonucleotide ZC21,076

<400> SEQUENCE: 24

cgttgctgct gctgctacta ctg                                           23


<210> SEQ ID NO 25
<211> LENGTH: 24
<212> TYPE: DNA
<213> ORGANISM: Artificial Sequence
<220> FEATURE:
<223> OTHER INFORMATION: oligonucleotide ZC21,074

<400> SEQUENCE: 25

gccgtagtgg gtttctatgt atcc                                          24


<210> SEQ ID NO 26
<211> LENGTH: 18
<212> TYPE: DNA
<213> ORGANISM: Artificial Sequence
<220> FEATURE:
<223> OTHER INFORMATION: oligonucleotide ZC21,075

<400> SEQUENCE: 26

tcggcggctg ctaaatgg                                                 18
```